(12) United States Patent
Makriyannis et al.

(10) Patent No.: US 7,329,651 B2
(45) Date of Patent: Feb. 12, 2008

(54) CANNABIMIMETIC LIGANDS

(75) Inventors: Alexandros Makriyannis, Mystic, CT (US); Hongfeng Deng, Acton, MA (US)

(73) Assignee: University of Connecticut, Farmington, CT (US)

( * ) Notice: Subject to any disclaimer, the term of this patent is extended or adjusted under 35 U.S.C. 154(b) by 253 days.

(21) Appl. No.: 10/466,403

(22) PCT Filed: Jan. 25, 2002

(86) PCT No.: PCT/US02/02157

§ 371 (c)(1), (2), (4) Date: Oct. 31, 2003

(87) PCT Pub. No.: WO02/058636

PCT Pub. Date: Aug. 1, 2002

(65) Prior Publication Data

US 2004/0077649 A1   Apr. 22, 2004

Related U.S. Application Data

(60) Provisional application No. 60/264,385, filed on Jan. 26, 2001.

(51) Int. Cl.
- C07D 257/08 (2006.01)
- A61K 31/395 (2006.01)
- A61P 3/04 (2006.01)

(52) U.S. Cl. .................................. 514/183; 544/179
(58) Field of Classification Search ................ 544/179; 514/183
See application file for complete search history.

(56) References Cited

U.S. PATENT DOCUMENTS

| | | |
|---|---|---|
| 3,041,343 A | 6/1962 | Jucker et al. |
| 3,465,024 A | 9/1969 | Brownstein et al. |
| 3,573,327 A | 3/1971 | Miyano |
| 3,577,458 A | 5/1971 | Brownstein et al. |
| 3,656,906 A | 4/1972 | Bullock |
| 3,838,131 A | 9/1974 | Gauthier |
| 3,886,184 A | 5/1975 | Matsumoto et al. |
| 3,897,306 A | 7/1975 | Vidic |
| 3,915,996 A | 10/1975 | Wright |
| 3,928,598 A | 12/1975 | Archer |
| 3,944,673 A | 3/1976 | Archer |
| 3,946,029 A | 3/1976 | Descamps et al. |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan et al. |
| 4,176,233 A | 11/1979 | Archer et al. |
| 4,179,517 A | 12/1979 | Mechoulam |
| 4,188,495 A | 2/1980 | Althuis et al. |
| 4,208,351 A | 6/1980 | Archer et al. |
| 4,278,603 A | 7/1981 | Thakkar et al. |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |
| 4,758,597 A | 7/1988 | Martin et al. |
| 4,812,457 A | 3/1989 | Narumiya |
| 4,876,276 A | 10/1989 | Mechoulam |
| 4,885,295 A | 12/1989 | Bell et al. |
| 5,053,548 A | 10/1991 | Tanaka et al. |
| 5,068,234 A | 11/1991 | D'Ambra et al. |
| 5,147,876 A | 9/1992 | Mitsuyuki et al. |
| 5,223,510 A | 6/1993 | Gubin et al. |
| 5,284,867 A | 2/1994 | Kloog |
| 5,324,737 A | 6/1994 | D'Ambra et al. |
| 5,434,295 A | 7/1995 | Mechoulam et al. |
| 5,440,052 A | 8/1995 | Makriyannis et al. |
| 5,462,960 A | 10/1995 | Barth et al. |
| 5,489,580 A | 2/1996 | Makriyannis et al. |
| 5,521,215 A | 5/1996 | Mechoulam |
| 5,532,237 A | 7/1996 | Gallant et al. |
| 5,538,993 A | 7/1996 | Mechoulam |

(Continued)

FOREIGN PATENT DOCUMENTS

EP    0276732    8/1988

(Continued)

OTHER PUBLICATIONS

Cecil Textbook of Medicine, edited by Bennet, J.C., and Plum F., 20th edition, vol. 1, 1004-1010, 1996.*
Petrocellis et al., British Journal of Pharmacology, 141, 765-774, 2004.*
Black, Curr. Opin.. Investig. Drugs 5(4): 389-394, 2004.*
Pertwee R.G., Expert Opinion on Investigational Drugs, 9(7): 1553-1571, 2000.*
Croce et al., J. Heterocyclic. Chem., 15, 515-517, 1978.*
Croce et al., J. C.S. Perkin Trans. I., 330-332, 1978.*

(Continued)

*Primary Examiner*—Venkataraman Balasubramanian
(74) *Attorney, Agent, or Firm*—Alix, Yale & Ristas, LLP

(57) ABSTRACT

Disclosed are heterocyclic compounds and methods for their manufacture. The disclosed compounds are surprisingly potent and selective cannabinoids. Also disclosed are methods of using the disclosed compounds, including use of the disclosed compounds to stimulate a cannabinoid receptor, to provide a physiological effect in an animal or individual and to treat a condition in an animal or individual.

12 Claims, No Drawings

U.S. PATENT DOCUMENTS

| | | | |
|---|---|---|---|
| 5,576,436 | A | 11/1996 | McCabe et al. |
| 5,605,906 | A | 2/1997 | Lau |
| 5,607,933 | A | 3/1997 | D'Ambra et al. |
| 5,618,955 | A | 4/1997 | Mechoulam et al. |
| 5,624,941 | A | 4/1997 | Barth et al. |
| 5,631,297 | A | 5/1997 | Pate et al. |
| 5,635,530 | A | 6/1997 | Mechoulam |
| 5,688,825 | A | 11/1997 | Makriyannis et al. |
| 5,744,459 | A | 4/1998 | Makriyannis et al. |
| 5,747,524 | A | 5/1998 | Cullinan et al. |
| 5,804,601 | A | 9/1998 | Kato et al. |
| 5,817,651 | A | 10/1998 | D'Ambra et al. |
| 5,872,148 | A | 2/1999 | Makriyannis et al. |
| 5,874,459 | A | 2/1999 | Makriyannis et al. |
| 5,925,628 | A | 7/1999 | Lee et al. |
| 5,925,768 | A | 7/1999 | Barth et al. |
| 5,932,610 | A | 8/1999 | Shohami et al. |
| 5,939,429 | A | 8/1999 | Kunos et al. |
| 5,948,777 | A | 9/1999 | Bender et al. |
| 6,013,648 | A | 1/2000 | Rinaldi et al. |
| 6,028,084 | A | 2/2000 | Barth et al. |
| 6,096,740 | A | 8/2000 | Mechoulam |
| 6,127,399 | A | 10/2000 | Yuan |
| 6,166,066 | A | 12/2000 | Makriyannis et al. |
| 6,284,788 | B1 | 9/2001 | Mittendorf et al. |
| 6,391,909 | B1 | 5/2002 | Makriyannis et al. |
| 6,579,900 | B2 | 6/2003 | Makriyannis et al. |
| 6,610,737 | B1 | 8/2003 | Garzon et al. |
| 6,864,291 | B1 | 3/2005 | Fride et al. |
| 2002/0119972 | A1 | 8/2002 | Leftheris et al. |
| 2002/0173528 | A1 | 11/2002 | Fride et al. |
| 2003/0120094 | A1 | 6/2003 | Makriyannis et al. |
| 2003/0149082 | A1 | 8/2003 | Makriyannis et al. |
| 2004/0077851 | A1 | 4/2004 | Makriyannis et al. |
| 2004/0087590 | A1 | 5/2004 | Makriyannis et al. |
| 2004/0192667 | A1 | 9/2004 | Makriyannis et al. |
| 2004/0236101 | A1 | 11/2004 | Makriyannis et al. |
| 2004/0236116 | A1 | 11/2004 | Makriyannis et al. |
| 2005/0020679 | A1 | 1/2005 | Makriyannis et al. |
| 2005/0074408 | A1 | 4/2005 | Makriyannis et al. |

FOREIGN PATENT DOCUMENTS

| | | |
|---|---|---|
| EP | 0444451 | 9/1991 |
| EP | 0471609 | 6/1993 |
| EP | 0576357 | 12/1993 |
| EP | 0737671 | 10/1996 |
| EP | 0860168 | 9/2001 |
| FR | 2240003 | 5/1975 |
| FR | 2735774 | 1/2000 |
| GB | 2027021 A | 2/1980 |
| IL | 1995-113228 | 9/1999 |
| JP | 57098228 | 6/1982 |
| JP | 2304080 | 12/1990 |
| WO | WO 94/12466 | 6/1994 |
| WO | WO 97/00860 | 1/1997 |
| WO | WO 97/21682 | 6/1997 |
| WO | WO 99/57106 | 11/1999 |
| WO | WO 99/57107 | 11/1999 |
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 02/060447 | 8/2002 |
| WO | WO 03/005960 | 1/2003 |
| WO | WO 03/020217 | 3/2003 |
| WO | WO 03/035005 | 5/2003 |
| WO | WO 03/063758 | 8/2003 |
| WO | WO 03/064359 | 8/2003 |

OTHER PUBLICATIONS

Molteni et al., J. C.S. Perkin Trans. I., 3742-3745, 2000.*

Tewari et al., Tetrahedron, 39(1), 129-136, 1983.*

Petrov, M.L., Terent'eva, N.A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-Phenylnitrilimine"; Zhurnal Organicheskoi Khimii; 29(7); 1372-1378; (1993) (abstract only).

Lozinsjii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

Shawali, A.S., Albar, H.A.; "Kinetics and mechanism of dehydrochlorination of N-aryl-C-ethoxycarbonyl formohydrazidoyl chlorides"; Canadian Journal Of Chemistry; 64(5); 871-875; 1986 (abstract only).

Bodnar, V.N., Lozinskii, M.O., Pel'kis, P.S.; "Synthesis fo 2,5-disubstituted 1,3,4-oxadiazoles and 1,4-dihydro-1,2,4,5-tetrazines"; Ukrainskii Khimicheskii Zhurnal (Russian Edition); 48(12); 1308-1311; 1982 (abstract only).

Santus Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

Supplementary Partial European Search Report for Application No. 02 70 7564 dated Jan. 22, 2004, pp. 1-4.

U.S. Appl. No. 09/600,786, filed Nov. 24, 1999, Makriyannis et al (copy not included, this is the U.S. National Phase of the Int'l Application published as WO 00/32200 enclosed herewith).

U.S. Appl. No. 09/698,071, filed Oct. 30, 2000, Fride et al, (copy not included, this is the parent application for US Publication No. 2002/0173528, enclosed herewith).

U.S. Appl. No. 09/701,989, filed Jun. 9, 1999, Makriyannis et al (copy not included, this is the U.S. National Phase of the Int'l Application published as WO 99/64389 enclosed herewith).

U.S. Appl. No. 10/110,865, filed Oct. 18, 2000, 1 Makriyannis et al (copy not included, this is the U.S. National Phase of the Int'l Application published as WO 01/28497 enclosed herewith).

U.S. Appl. No. 10/110,830, filed Oct. 18, 2000, Makriyannis et al (copy not included, this is the U.S. National Phase of the Int'l Application published as WO 01/28329 enclosed herewith).

U.S. Appl. No. 10/110,812, filed Oct. 18, 2000, Makriyannis et al (copy not included, this is the U.S. National Phase of the Int'l Application published as WO 01/28498 enclosed herewith).

U.S. Appl. No. 10/110,862, filed Oct. 18, 2000, Makriyannis et al (copy not included, this is the U.S. National Phase of the Int'l Application published as WO 01/29007 enclosed herewith).

U.S. Appl. No. 10/111,059, filed Oct. 18, 2000, Makriyannis et al (copy not included, this is the U.S. National Phase of the Int'l Application published as WO 01/28557 enclosed herewith).

U.S. Appl. No. 10/483,482, filed Jul. 11, 2002, Makriyannis et al (copy not included, this is the U.S. National Phase of the Int'l Application published as WO 03/005960 enclosed herewith).

U.S. Appl. No. 10/493,093, filed Oct. 28, 2002, Makriyannis et al (copy not included, this is the U.S. National Phase of the Int'l Application published as WO 03/35005 enclosed herewith).

U.S. Appl. No. 10/647,544, filed Aug. 25, 2003, Makriyannis et al.

U.S. Appl. No. 10/790,498, filed Mar. 1, 2004, 1 Makriyannis et al.

Abadji V., Lin S., Taha G., Griffin G., Stevenson L.A., Pertwee R.G., Makriyannis A.; "(R)-Methanadamide: a chiral novel anandamide possessing higher potency and metabolic stability"; J. Med. Chem.; 37(12); 1889-1893; 1994; CODEN: JMCMAR; ISSN: 0022-2623; XP002040932.

Alo, B.I.; Kandil, A.; Patil, P. A.; Sharp, M. J.; Siddiqui, M. A.; and Snieckus, V. Sequential Directed Ortho Metalation-Boronic Acid Cross-Coupling Reactions. A general Regiospecific Route to Oxygenated Dibenzo[b,d]pyran-6-ones Related to Ellagic Acid, J. Org. Chem. 1991, 56, 3763-3768.

Archer et al; "cannabinoids, synthesis approaches to 9-ketocannabinoids."; J. Org. Chem.; vol. 42; No. 13; 2277-2284; (1977).

Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).

Barnett-Norris et al; "Exploration of biologically relevant conformations of anandamide, . . . "; J. Med. Chem.; vol. 41; 4861-4872; 1998.

Beak, P.; and Brown, R A., The Tertiary Amide as an Effective Director of Ortho Lithiation, J. Org. Chem. 1982, 47, 34-36.

Belgaonkar et al; "synthesius of isocoumarins"; Indian J. Chem; vol. 13; No. 4; 336-338; 1975 (abstract only).

Beltramo M., Stella N., Calignano A., Lin S. Y., Makriyannis A., Piomelli D; "Identification and Functional Role of High Affinity Anandamide Transport"; The Neurosciences Institute (1 page).

Berdyshev EV, Cannabinoid receptors and the regulation of immune response. Chem Phys Lipids. Nov. 2000; 108(1-2):169-90.

Berglund et al; "Structural requirements for arachidonylethanolamide interaction with CB1 and CB2 cannabinoid receptors: . . . "; Prostanglandins, leukotrienes ands essential fatty acids; 59(2); 111-118; (1998). (abstract only).

Bracey, M et al, Structural Adaptations in a Membrane Enzyme That Terminates Endocannabinoid Signaling. Science 2002; 298(5599): 1793-1796.

Brenneisen R, Pgli A, Elsohly MA, Henn V. Spiess Y: The effect of orally and rectally administered ∆9—tetrahydrocannabinol on spasticity, a pilot study with 2 patients. Int. J. Clin Pharmacol Ther. (1996) 34:446-452. (abstract only).

Brotchie JM: *Adjuncts to dopamine replacement a pragmatic approach to reducing the problem of dyskinesia in Parkinson's disease. Mov. Disord.* (1998)13:871-876.

Brown et al; "Synthesis and hydroboration of (-)-2-phenylapopinene, Comparison of mono(2-phenylapoisopinocampheyl)borane with its 2-methyl and 2-ethyl analogues for the chiral hydroboration of representative alkenes"; J. Org. Chem.; 55(4); 1217-1223; (1990).

Buckley NE, McCoy KI, Mpzey E et al, "Immunomodulation by cannabinoids is absent in mice deficient for the cannabinoid CB2 receptor"; Eur. J Pharmacol (2000) 396:141-149.

Burstein et al; "detection of cannabinoid receptors . . . "; Biochem. Biophys. Res. Commun.; vol. 176(1); 492-497; 1991 (abstract only).

Busch-Peterson et al; "Unsaturated side chain beta-11-hydroxyhexahydrocannabinol analogs"; J. Med. Chem.; 39; 3790-3796; (1996).

Calignano A, La Rana G. Diuffrida A, Piomelli D; "Control of pain initiation by endogenous cannabinoids"; Nature (1998) 394:277-291. (abstract only).

Calignano A., La Rana G., Beltramo, M., Makriyannis A., Piomelli D; "Potentiation of Anandamide Hypotension by the Transport Zinhibitor, AM404"; Eur. J. Pharmacol.; 1997; 337 R1-R2.

Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7-R8.

Campbell FA et al; "Are cannabinoids an effective and safe treatment option in the management of pain? A qualitative systematic review"; BMJ. Jul. 7, 2001;323(7303):13-6.

Charalambous A. et al; "5'-azido ∆8-THC: A Novel Photoaffinity Label for the Cannabinoid Receptor"; J. Med. Chem., 35, 3076-3079 (1992).

Charalambous A. et al; "Pharmacological evaluation of halogenated . . . "; Pharmacol. Biochem. Behav.; vol. 40; No. 3; 509-512; 1991.

Cheng et al; "Relationship Between the Inhibition Constant (Ki) and the concentration on Inhibitor which causes 50% Inhibition (IC50) of an Enzymatic Reaction"; Biochem. Pharmacol., 22, 3099-3102, (1973) (abstract only).

Cherest M., Luscindi X.; "The action of acetyl chloride and of acetic anhydride on the lithium nitronate salt of 2-phenylnitroethane . . . "; Tetrahedron; 42(14); 3825-3840; 1986; in French with English abstract.

Cherest M., Lusinchi X.; "A novel electrophilic N-amidation via electron deficient complexes: action of ferric chloride on N-acetyloxyamides"; Tetrahedron Letters; 30(6); 715-718; 1989.

Colombo G, Agabio R, Diaz G. et al; "Appetite suppression and weight loss after the cannabinoid antagonist SR141716"; Life Sci. (1998) 63-PL13-PL117. (abstract only).

Compton D.R. et al; *J. Pharmacol. Exp. Ther.*; 260; 201-209; 1992.

Compton et al; "Synthesis and pharmacological evaluation of ether and related analogues of delta8-. delta9- and delta9,11-tetrahydrocannabinol"; J. Med. Chem; vol. 34; No. 11; 3310-3316; 1991.

Consroe P, Musty R, Rein J, Tillery W, Pertwee R; "The perceived effects of smoked cannabis on patents with multiple sclerosis"; Eur. Neurol. (1997) 38-44-48. (abstract only).

Coxon et al; "Derivatives of nopinone"; Aust. J. Chem.; 23; 1069-1071; (1970) (astract only).

Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.

D'Ambra et al; "C-attached aminoalkylindoles: potent cannabinoid mimetics"; Bioorg. & Med. Chem. Lett., 1996, 6(1), 17-22.

D'Amour F.E., Smith D.L.; *J. Pharmacol. Exp. Ther.*; 72; 74-79; 1941.

Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.

DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375-8380.

Desarnaud F., Cadas H., Piomelli D.; "Anandamide amidohydrolase activity in rat brain microsomes"; J. Biol. Chem.; 270; 6030-6035; (1995).

Deutsch D.G. et al; "Fatty acid sulfonyl fluorides inhibit anandamide metabolism and bind to cannabinoid receptor"; Biochem. Biophys. Res. Commun. 231(1); 217-221; 1997; CODEN: BBRCA9; ISSN:0006-291X; XP002040933.

Deutsch D.G., Chin S.A.; "Enzymatic synthesis and degradation of anandamide, a cannabinoid receptor agonist"; Biochemical Pharmacology; 46(5); 791-796; 1993.

Devane, W.A. et al; "Determination and Characterization of a Cannabinoid Receptor in a Rat Brain"; Mol. Pharmacol., 34, 605-613 (1988). (abstract only).

Di Marzo, V., Melck, D., Bisogno, T., DePetrocellis, L.; "Endocannabinoids: endogenous cannabinoid receptor ligands with neuromodulatory action"; Trends Neurosci. (1998) 21:521-528.

Dodd, P.R. et al, *A Rapid Method for Preparing Synaptosomes: Comparison with Alternative Procedures, Brain Res.*, 226, 107-118 (1981).

Dominiami et al; "Synthesis of 5-(tert-Alkyl)resorcinols"; J. Org. Chem. 42(2); 344-346; (1977).

Drake et al, "classical/nonclassical hybrid cannabinoids"; J. Med. Chem.; vol. 41(19); 3596-3608 (1998).

Edery et al; "Activity of novel aminocannabinoids in baboons"; J. Med. Chem.; 27; 1370-1373 (1984).

Eissenstat et al; "Aminoalkylindoles: structure-activity relationships of novel cannabinoid mimetics"; J. Med. Chem. 1995, vol. 38, No. 16, pp. 3094-3105; XP 000651090.

Fahrenholtz, K. E., Lurie, M. and Kierstead, AR. W.; "The Total Synthesis of dl-∆9-Tetrahydrocannabinol and Four of Its Isomers"; J. Amer. Chem. Soc. 1967, 89(23), 5934-5941.

Fahrenholtz; "The synthesis of 2 metabolites of (-)-delta eight-tetrahydrocannabinol"; J. Org. Chem.; vol. 37(13); 1972; XP002111824.

Fride, E. & Mechoulam, R.; "Pharmacological activity of the cannabinoid receptor agonist, anandamide, a brain constituent"; European Journal of Pharmacology, vol. 231; 313-314; 1993.

Galiegue S et al. ; "Expression of central and peripheral cannabinoid receptors in human immune tissues and leukocyte subpopulations"; Eur J Biochem.; Aug. 15, 1995;232(1):54-61. (abstract only).

Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189-194.

Gold et al; "A comparison of the discriminative stimulus properties of delta9-tetrahydrocannabinol and CP 55,940 in rats and rhesus monkeys"; J. Pharmacol. Exp. Ther.; vol. 262(2); 479-486; 1992.

Green K. *Marijuana smoking vs. cannabinoids for glaucoma therapy.* Arch. Ophibalmol. (Feb. 1998) 433-1437.

Hampson, A.J., Grimaldi M. Axpirod J. Wink D; "Cannabidiol and (−) Δ9 tetrahydrocannabinol are neuroprotective antioxidants"; Proc. Natl Acad Sci. USA (Jul. 1998) 95; 8268-8273.

Hargreaves, K. et al; "A new sensitive method for measuring thermal nociception in cutaneous hyperalgesia"; Pain; 32; 77-88; (1988) (abstract only).

Hemming M, Yellowlees PM; *"Effective treatment of Tourette's syndrome with marijuana"; J. Psychopharmacol*, (1993) 7:389-391.

Herzberg U, Eliav E, Bennett GJ, Kopin IJ; "The analgesic effects of R(+) WIN 55,212-2 mesylate, a high affinity cannabinoid agonist in a rat model of neuropathic pain"; Neurosci. Letts. (1997) 221; 157-160.

Hillard C. J., Edgemond, W. S., Jarrahian W., Campbell, W. B; "Accumulation of N-Arachidonoylethanolamine (Anandamide) into Cerebellar Granule Cells Occurs via Facilitated Diffusion"; Journal of Neurochemistry; 69; 631-638 (1997).

Horrevoets A.J.G et al; "Inactivation of *Escherichia coli* outer membrane phospholipase A by the affinity label hexadecanesulfonyl fluoride"; Eur. J. Biochem.; 198; 247-253; 1991.

Horrevoets A.J.G et al; "Inactivation of reconstituted *Escherichia coli* outer membrane phospholipase A by membrane-perturbing peptides results in an increased reactivity towards the affinity label hexadecanesulfonyl fluoride"; Eur. J. Biochem.; 198; 255-261; 1991.

1 Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

Howlett et al; "Stereochemical effects of 11-OH-delta 8 tetrahydrocannabinol-dimethylheptyl to inhibit adenylate cyclase and bind to the cannabinoid receptor"; Neuropharmacology; vol. 29(2); 161-165; 1990.

Huffman et al; "3-(1', 1'-dimethylbutyl)—deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydrocannabinols"; tetrahedron; vol. 51(4); 1017-1032; (1995).

Huffman et al; "Synthesis of 5', 11 dihydroxy delta 8 tetrahydrocannabinol"; Tetrahedron, vol. 53(39), pp. 13295-13306 (1997).

Huffman et al; "Synthesis of a tetracyclic, conformationally constrained analogue of delta8-THC"; Bioorganic & Medicinal Chemistry; vol. 6(12); 2281-2288; 1998; XP002123230.

Huffman et al; "Synthesis of both enantiomers of Nabilone from a common intermediate. Enantiodivergent synthesis of cannabinoids"; J. Org. Chem.; 1991, 56, 2081-2086.

Joy JE, Wagtson SJ, Benson JA; *"Marijuana and Medicine Assessing the Science Base"*; National Academy Press, Washington, DC, USA (1999).

Kaminski NE; "Regulation of the cAMP cascade, gene expression and immune function by cannabinoid receptors"; J Neuroimmunol. Mar. 15, 1998;83(1-2):124-32.

Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515-4519; (1996).

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug. 1998; 19(8):373-81.

Koutek B. et al; "Inhibitors of arachidonyl ethanolamide hydrolysis"; J. Biol. Chem.; 269(37); 22937-40; 1994; CODEN: JBCHA3; ISSN: 0021-9258.

Kumar RN, et al; "Pharmacological actions and therapeutic uses of cannabis and cannabinoids"; Anesthesia, 2001, 56: 1059-1068 (abstract only).

1 Lan, R et al; "Structure activity relationships of pyrazole derivatives as cannabinoid receptor antagonists"; J. Med. Chem.; vol. 42(4); 769-776; (1999).

Lavalle et al; "Efficient conversion of (1R, 5R)-(+)-alpha-pinene to (1S, 5R)-(−)-nopinene"; J. Org. Chem.; vol. 51(8); 1362-1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

Loev, B., Bender, P. E., Dowalo, F., Macko, E., and Fowler, P.; "Cannabinoids. Structure-Activity Studies Related to 1,2-Dimethylheptyl Derivatives"; J. Med. Chem.; vol. 16(11); 1200-1206; 1973.

Ludt, R.E. et al; "A comparison of the synthetic utility of n-butyllithium and lithium diisopropylamide in the metalations of N,N-dialkyltouamides"; J. Org. Chem.; 38(9); 1668-1674 (1973).

Maccarron M., *Endocannabinoids and their actions. Vitamins and Hormones* 2002;65:225-255.

Mackie K., Devane W.A., Hille B.; "Anandamide, an endogenous cannabinoid, inhibits calcium currents as a partial agonist in N18 neuroblastoma cells"; Mol. Pharmacol; 44; 498-0503 (1993).

Markwell et al; *Anal. Biochem.*; 87:206 (1978).

Martin et al; "Behavioral, biochemical, and molecular modeling evaluations of cannabinoid analogs"; Pharmacol. Biochem. Behav.; vol. 40(3); 471-478; 1991.

Martyn CN. Illis LS, Thom J.; "Nabilone in the treatment of multiple sclerosis"; Lancet (1995) vol. 345; pp. 579.

Matsumoto et al; "Cannabinoids 1.1-amino-and 1 mercapto-7,8,9,10-tetrahydro-6h-dibenzo[b,d]pyrans"; J. of Med. Chem.; vol. 20(1); 17-24; 1977; XP00211825.

Maurer M, Henn V, Dittrich A, Hofmann A. *Delta-9-tetrahydrocannabinol shows antispastic and analgesic effects in a single case double-blind trial. Eur. Arch. Psychiat. Clin. Neurosci.* (1990), Z40:1-4.

Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 1996; XP002111823.

Mechoulam et al; "Stereochemical Requirements for cannabinoid activity"; J. Med. Chem.; 23(10); 1068-1072; (1980).

Mechoulam et al; "Synthesis of the individual, pharmacologically distinct, enantiomers of a tetrahydrocannabinol derivative"; Tetrahedron Asymmetry; 1: 311-314; (1990) (abstract only).

Mechoulam et al; *Tetrahedron Asymmetry*; 1: 315-318; (1990).

Mechoulam, *"Cannabinoids as therapeutic agents"*; CRC press, 1986.

Meltzer et al; "An improved synthesis of cannabinol and cannabiorcol"; Synthesis; 1981:985 (1981).

Melvin et al; *drug design and discovery*; 13; 155-166 (1995).

Melvin et al; "Structure-activity relationships for cannabinoid receptor-binding and analgesic activity: studies of bicyclic cannabinoid analogs"; Mol. Pharmacol.; 44(5); 1008-1015 (1993).

Merck Index; 11th edition; "Tetrahydrocannabinols" compound No. 9142; 1989.

Morgan Dr: *Therapeutic Uses of Cannabis. Harwood Academic Publishers, Amsterdam.* (1997).

Morris, S,; Mechoulam, R.; and Irene, Y., *Halogenation of phenols and Phenyl ethers with Potassium Halides in the Presence of 18-Crown-6 on Oxidation with m-Chloroperbenzoic Acid, J. Chem. Soc., Perkin Trans.* 1 1987, 1423-1427.

Muller-Vahl KB, Kolbe H, Schneider U, Emrich, HM Cannabis *in movement disorders. Porsch. Kompicmentarmed* (1999) 6 (suppl. 3) 23-27.

Muller-Vahl KB, Schneider U, Kolbe H, Emrich, HM. *Treatment of Tourette's syndrome with delta-9-tetrahydrocannabinol. Am. J. Psychiat.* (1999) 156-195.

Nahas G, *Marijuana and Medicine*; 1999, *Human Press Inc.*, Totowa, NJ.

Neunhoeffer O., Gottschlich R.; "Acylating activity of O-acylated hydroxylamine derivatives"; Justus Liebigs Ann. Chem.; 736; 100-109; 1970; in German with English abstract.

Novak, J et al; Cannabis, part 27, synthesis of 8-, 10- and 11-oxygenated cannabinoids; J. Chem. Soc. Perkin Trans.; 2867-2871; (1983) (abstract only).

Nye et al; "High affinity cannabinoid binding sites in brain membranes labelled with [H]-5'-trimethylammonium delta8-tetrahydrocannabinol"; J. Pharmacol. Exp. Ther.; vol. 234(3); 784-791; 1985.

Pacheco M, et al; "Aminoalkylindoles: Actions On Specific G-Protein-Linked Receptors"; J. Pharmacol. Exp. Ther.; vol. 257, No. 1, pp. 170-183 and 172 Table (1991).

Palmer et al; *current pharmaceutical design*; 6; 1381-1397; (2000).

Papahatjis et al; "A new ring-forming methodology for the synthesis of conformationally constrained bioactive molecules"; Chemistry Letters, 192; (2001).

Papahatjis et al; "Pharmacophoric requirements for cannabinoid side chains: multiple bond and C1'-substituted delta8-tetrahydrocannabinols"; J. Med. Chem.; 41(7); 1195-1200; (1998).

Pertwee et al; "AM630, a competitive cannabinoid receptor agonist"; Life Sci. 1995, 56(23/24), 1949-1955; XP 000653566.

Pertwee et al; "Pharmacological characterization of three novel cannabinoid receptor agonists in the mouse isolated vas deferens"; Eur. J. Pharmacol. 1995, 284, 241-247; XP-001041044.

Pertwee et al; *Br. J. Pharmacol.*; 105; 980 1992.

Pertwee; Pharmacology of cannabinoid CB1 and CB2 receptors; Pharmacol. Ther., vol. 74(2); pp. 129-180; (1997); XP002226467.

Pinnegan-Ling D, Musty R.; *Marinol and phantom limb pain: a case study. Proc Inv. Cannabinoid Rea. Sec.* (1994):53.

Piomelli D., Beltramo M., Glasnapp S., Lin S.Y., Goutopoulos A., Xiw X-Q., Makriyannis A.; "Structural determinants for recognition and translocation by the anandamide transporter"; Proc. Natl. Acad. Sci. USA; 96; 5802-5807; (1999).

Pitt et al; "The synthesis of Deuterium, carbon-14 and carrier free tritium labelled cannabinoids"; Journal of Labellled Compounds; vol. 11(4); 551-575; 1975; XP002123229.

Porreca F., Mosberg H.I., Hurst R., Hruby V.J., Burks T.F.; *"Roles of mu, delta and kappa opiod receptors in spinal and supraspinal mediation of gastrointestinal transit effects and hot-plate analgesia in the mouse"; J. Pharmacol. Exp. Ther.*; 230; 341-348; (1994).

Razdan et al; "Drugs derived from cannabinoids. 6. .Synthesis of cyclic analogues of dimethylheptylpyran", J. Med. Chem.; vol. 19(5); 719-721; 1976 (abstract only).

Reggio et al; "Characterization of a region of steric interference at the cannabinoid receptor using the active analog approach"; J. Med. Chem. United States; vol. 36(12); 1761-1771; 1993.

Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228-3233.

Rice AS. *Cannabinoids and pain. Curr Opin Investig Drugs.* Mar. 2001;2(3):399-414.

Richardson JD, Aanonsen I, Hargreaves KM; "Antihyperalgesic effects of a spinal cannabinoids"; Eur. J. Pharmacol. (1998) 346:145-153.

Richardson JD, Kilo S. Hargreaves KM; "Cannabinoids reduce dryperalgesia and inflammation via interaction with peripheral CB1 receptors"; Pain (1998) 75:111-119.

1 Rinaldi-Carmona et al; "Biochemical and pharmacological characterization of SR141716A, the first potent and selective brain cannabinoid receptor antagonist"; Life Sci.; vol. 56(23/24); 1941-1947 (1995).

1 Rinaldi-Carmona et al; "SR141716A, a potent and selective antagonist of the brain cannabinoid receptor"; FEBS Lett.; 350; 240-244; (1994).

Rompp Chemie Lexikon; Falbe and Regitz; "band 1-A-C1, 8"; Aufl, Thieme Verlag; Stuttgart, S 569-570; 1989.

Schatz AR et al; "Cannabinoid receptors CB1 and CB2: a characterization of expression and adenylate cyclase modulation within the immune system"; Toxicol Appl Pharmacol. Feb. 1997; 142(2):278-87.

Schuel, H., Burkman, L.J., Picone, R.P., Bo, T., Makriyannis, A., *Cannabinoid receptors in human sperm. Mol. Biol. Cell.*, (1997) (8), 325a.

Serdarevich B., Caroll K.K., *"Synthesis and characterization of 1- and 2- monoglycerides of anteiso fatty acids"; J. Lipid Res.*; 7; 277-284; (1966).

Shen M. Thayer SA: *Cannabinoid receptor agonists protect cultured rat hippocampal neurons from excitotoxicity. Mol. Pharmacol* (1996) 54:459-462.

Shim et al; "Three-dimensional quantitative structure-activity relationship study of the cannabimimetic (aminoalkyl)indoles using comparative molecular field analysis"; J. Med. Chem.; 1998, 41(23); 4521-4532; XP-002212407.

Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.

Simiand J, Keane M, Keane PE, Soubrie P: *SR 141716, A CB1 cannabinoid receptor antagonist, selectivity reduces sweet food intake in marmoset. Behav. Pharmacol* (1998) 9:179-181.

Smith P.B. et al; "The pharmacological activity of anandamide, a putative endogenous cannabinoid, in mice" ; Journal of Pharmacology and Experimental Therapeutics; vol. 270(1):219-227; 1994.

Tetko, I. V. et al; "Volume Learning Algoritm Artificial Neural Networks For 3D QSAR Studies"; J. Med. Chem.; vol. 44, No. 15 (2001) pp. 2411-2420, 2413, 2414 Table 1.

Terranova J-P, Storme J-J Lafon N et al; *"Improvement of memory in rodents by the selective CB1 cannabinoid receptor antagonist, SR 141716"; Psycho-pharmacol* (1996) 126:165-172.

Tius et al; "Conformationally restricted hybrids of CP-55,940 and HHC: Stereoselective synthesis and activity"; Tetrahedron; 50 (9); 2671-2680; (1994) (abstract only).

Twitchell, W. et al; "Cannabinoids inhibit N- and P/Q type calcium channels in cultured rat hippocampal neurons"; Journal of Neurophysiology; 78(1); 43-50; 1997 (abstract only).

Ueda, N., *Endocannabinoid hydrolases. Prostaglandins & Other Lipid Mediators 2002*;68-69:521-534.

Vogel Z., Barg J., Levy R., Saya D., Heldman E., Mechoulam R.; *"Anandamide, a brain endogenous compound, interacts specifically with cannabinoid receptors and inhibits adenylate cyclase"; J. Neurochem.*; 61(1) 352-355; (1993).

Wagner JA, Varga K, Jarai Z, Kunos G; *'Mesenteric vasodialtion mediated by endothelia anandamide receptors'; Hypertension* (1999) 33:429-434.

Watanabe, T.; Miyaura, N.; and Suzuki, A.; "Synthesis of Sterically Hindered Biaryls via the Palladium Catalyzed Cross-Coupling Reaction of Arylboronic Acids or their Esters with Haloarenes"; Synlett 1992, 207-210.

Wiley et al; "Structure activity relationships of indole and pyrrole derived cannabinoids"; J. Pharmacol. Exp. Ther. 1998, 285(3), 995-1004; XP-001097982.

Wilson et al; "9-nor-delta8-tetrahydrocannabinol, a cannabinoid of metabolic intersts"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydrohexahydrocannabinols. Synthesis, some behavioral and analgesic properties, and comparison with the tetrahydrocannabinols"; J. Med. Chem.; 19(9); 1165-1167; (1976).

Yamada et al; "(Aminoalkyl)indole isothiocyanates as potentiual electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1'-dimethylheptyl)hexahydrocannabinol: a high affinity cannabinoid agonist"; J. Med. Chem.; vol. 37(16); 2619-2622; (1994).

Yan Guo et al; "(−)-11-hydroxy-7'-isothiocyanato-1'-1'dimethylheptyl-delta8-THC: a novel probe for the cannabinoid receptor in the brain"; J. Med. Chem.; 37(23); 3867-3870; (1994).

Beltramo M., Piomelli D; "Anandamide Transport Inhibition by the Vanilloide Agonist Olvanil"; Europeean J. of Pharmacology; (1999); 364(1); 75-78 (abstract only).

Bodnar, V.N., Lozinskii, M.O., Pel'kis, P.S.; "Synthesis of 2,5-disubstituted 1,3,4-oxadiazoles and 1,4-dihydro-1,2,4,5-tetrazines"; Ukrainskii Khimicheskii Zhurnal (Russian Edition); 48(12); 1308-1311; 1982 (abstract only).

2 Brotchie JM: *Adjuncts to dopamine replacement a pragmatic approach to reducing the problem of dyskinesia in Parkinson's disease.* Mov. Disord. (1998)13:871-876. (abstract only).

2 Compton D.R. et al; "*Pharmacological Profile Of A Series Of Bicyclic Cannabinoid Analogs: Classification as Cannabimimetic Agents*"; J. Pharmacol. Exp. Ther.; 260; 201-209; 1992. (abstract only).

Di Marzo, V., Bisogno, T., Melck, D., Ross, R., Brockie, H., Stevenson, L., Pertwee, R., DePetrocellis, L., "Interactions between synthetic vanilloids and the endogenous cannabinoid system"; FEBS Letters; (1998); 437(3); 449-454. (abstract only).

2 Dodd, P.R. et al, *A Rapid Method for Preparing Synaptosomes: Comparison with Alternative Procedures, Brain Res.*, 226, 107-118 (1981). (abstract only).

Fisera, L., Kovac, J., Lesco, J., Smahovsky, V.; "Furan derivatives. Part CLVI. 1,3-dipolar cycloadditions of heterocycles. V. Reaction of C-acetyl-N-phenylnitrilimine with furan derivatives"; Chemicke Zvesti; 35(1); 93-104 1981 (abstract only).

2 Green K.; *"Marijuana smoking vs. cannabinoids for glaucoma therapy,"*; Arch. Ophthamol. (Nov. 1998) 116(11); 1433-1437. (abstract only).

Griffin, G., Wray, E. J., Tao, Q., McAllister, S. D., Rorrer, W. K., Aung, M., Martin, B. R., Abood, M. E.; "Evaluation of the cannabinoid CB2 receptor selective antagonist, SR144528: further evidence for cannabinoid CB2 receptor absence in the rat central nervous system"; European Journal of Pharmacology; (1999); vol. 377; 117-125.

Jbilo, O., Derocq, J., Segui, M., Le Fur, G., Casellas, P.; "Stimulation of peripheral cannabinoid receptor CB2 induces MCP-1 and IL-8 gene expression in human promyelocytic cell line HL60"; FEBS Letters; (1999); vol. 448; No. 21848; 273-277.

2 Joy JE, Wagtson SJ, Benson JA; *"Marijuana and Medicine Assessing the Science Base"*; National Academy Press, Washington, DC, USA (1999). (abstract only).

Lang, W. et al; "Substrate Specificity and Stereoselectivity of Rat Brain Microsomal Anandamide Amidohydrolase"; J. Med. Chem.; vol. 42(5); 896-902; (1999).

Lozinskii, M.O., Bodnar, V.N., Konovalikhin, S.V., D'yachenko, O.A., Atovmyan, L.O.;"Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

2 Maurer M, Henn V, Dittrich A, Hofmann A.; *"Delta-9-tetrahydrocannabinol shows antispastic and analgesic effects in a single case double-blind trial."*; Eur. Arch. Psychiat. Clin. Neurosci. (1990), 240:1-4. (abstract only).

Mechoulam et al; Structural Requirements for Binding of Anandamide Type Compounds to the Brain Cannabinoid Receptor; J. Med. Chem.; 1997; 40; 659-667.

2 Mechoulam et al; "*Synthesis of the individual, pharmacologically distinct, enantiomers of a tetrahydrocannabinol derivative*"; Tetrahedron Asymmetry; 1: 311-314; (1990). (abstract only).

Melck, D., Bisogno, T., DePetrocellis, L., Chuang, H., Julius, D., Bifulco, M., DiMarzo, V.; "Unsaturated Long-Chain N-Acyl-vanillyl-amides"; Biochemical and Biophysical Res. Commun.; (1999); 262(1); 275-284 (abstract only).

2 Melvin et al; "*Structure-Activity Relationships Defining the ACD-Tricyclic Cannabinoids Cannabinoid Receptor Binding and Analgesic Activity*"; Drug Design and Discovery; 13(2); 155-166 (1995). (abstract only).

2 Melvin et al; "*Structure-activity relationships for cannabinoid receptor-binding and analgesic activity: studies of bicyclic cannabinoid analogs*"; Mol. Pharmacol.; 44(5); 1008-1015 (1993). (abstract only).

Meschler, J. P., Kraichely, D. M., Wilken, G. H., Howlett, A. C.; "Inverse Agonist Properties of N-(Piperidin-1-yl)-5-(4-chlorophenyl)-1-(2,4-dichlorophenyl)-4-methyl-1H-pyrazole-3-carboxamide HCL (SR141716A) and 1-(2-Chlorophenyl)-4-cyano-5-(4-methoxyphenyl)-1H-pyrazole-3-carboxylic Acid Phenylamide (CP-272871) for the CB1 Cannabinoid Receptor"; Biochemical Pharmacology; (2000); vol. 60; No. 9; 1315-1322.

2 Muller-Vahl KB, Kolbe H, Schneider U, Emrich, HM Cannabis *in movement disorders. Porsch. Kompicmentarmed* (1999) 6 (*suppl. 3*) 23-27. (abstract only).

2 Muller-Vahl KB, Schneider U, Kolbe H, Emrich, HM.; "*Treatment of Tourette's syndrome with delta-9-tetrahydrocannabinol.*" Am. J. Psychiat.; (1999); 156(3); 495.

2 Palmer et al; "*Natural and Synthetic Endocannabinoids and Their Structure-Activity Relationships*"; Current Pharmaceutical Design; 6; 1381-1397; (2000).

2 Pertwee et al; "*Inhibitory effects of certain enantiomeric cannabinoids in the mouse vas deferens and the myenteric plexus preparation of guinea-pig small intestine*"; Br. J. Pharmacol.; 105(4); 980-984 (1992). (abstract only).

Pinto et al; Cannabinoid Receptor Binding and Agonist Activity of Amides and Esters of Arachidonic Acid; Mol. Pharmacol.; 1994; 46(3); 516-522. (abstract only).

2 Porreca F., Mosberg H.I., Hurst R., Hruby V.J., Burks T.F.; "*Roles of mu, delta and kappa opiod receptors in spinal and supraspinal mediation of gastrointestinal transit effects and hot-plate analgesia in the mouse*"; J. Pharmacol. Exp. Ther.; 230(2); 341-348; (1994). (abstract only).

Quere, L., Boigegrain, R., Jeanjean, F., Gully, D., Evrard, G., Durant, F.; "Structural requirements of non-peptide neurotensin receptor antagonists"; J. Chem Soc., Perkin Trans. 2, (1996); 2639-2646.

Razdan et al; "Pharmacological and Behavioral Evaluation of Alkylated Anandamide Analogs"; Life Sci.; 1995; 56(23-24); 2041-2048 (abstract only).

2 Rice AS. *Cannabinoids and pain. Curr Opin Investig Drugs.* Mar. 2001;2(3):399-414. (abstract only).

Santus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

2 Serdarevich B., Caroll K.K., "*Synthesis and characterization of 1- and 2- monoglycerides of anteiso fatty acids*"; J. Lipid Res.; 7; 277-284; (1966).

2 Shen M. Thayer SA: *Cannabinoid receptor agonists protect cultured rat hippocampal neurons from excitotoxicity.* Mol. Pharmacol (1996) 54:459-462.

2 Simiand J, Keane M, Keane PE, Soubrie P: *SR 141716, A CB1 cannabinoid receptor antagonist, selectively reduces sweet food intake in marmoset. Behav. Pharmacol* (1998) 9:179-181. (abstract only).

2 Terranova J-P, Storme J-J Lafon N et al; "*Improvement of memory in rodents by the selective CB1 cannabinoid receptor antagonist, SR 141716*"; Psycho-pharmacol (1996) 126:165-172 (abstract only).

2 Ueda, N., *Endocannabinoid hydrolases. Prostaglandins & Other Lipid Mediators* 2002;68-69:521-534 (abstract only).

2 Vogel Z., Barg J., Levy R., Saya D., Heldman E., Mechoulam R.; "*Anandamide, a brain endogenous compound, interacts specifically with cannabinoid receptors and inhibits adenylate cyclase*"; J. Neurochem.; 61(1) 352-355; (1993) (abstract only).

2 Wagner JA, Varga K, Jarai Z, Kunos G; "Mesenteric Vasodilation Mediated by Endothelia Anandamide Receptors"; Hypertension (1999) 33:429-434.

Supplementary Partial European Search Report for application No. 02 76 8751, pp. 1-2.

2 Archer et al; "cannabinoids, synthesis approaches to 9-ketocannabinoids."; J. Org. Chem.; vol. 42; No. 13; 2277-2284; (1977).

Hanus et al; "Two new unsaturated fatty acid ethanolamides in brain that bind to the cannabinoid receptor"; Journal of medicinal Chemistry; 36(20); 3032-3034; 1993.

Lang, W., Qin, C., Hill, W.A., Lin, S., Khanolkar, A.D., Makriyannis, A.; High-Performance Liquid Chromatographic Determination Of Anandamide Amidase Activity in Rat Brain Microsomes; Anal. Biochem; (1996), 238, 40-45 (abstract only).

Mechoulam et al; "Towards Cannabinoid drugs—Revisited"; Progress in Medicinal Chemistry; 35; 199-243; Jul. 3, 1998.

Sheskin, T. et al; Structural Requirements for Binding of Anandamide Type Compounds to the Brain Cannabinoid Receptor; J. Med. Chem.; 1997; 40; 659-667.

R.K. Bansal et al, "Reaction of N-Phenacyl or Substituted Phenacyl-pyridinium Bromide with 3-Pyridyldiazonium Chloride . . . ", *Indian Journal of Chemistry*, vol. 20B, Jun. 1981, pp. 503-504.

M. Girardot et al, "Direct Conversion of Heteroaromatic Esters to Methyl Ketones with Trimethylaluminum: . . . " *J. Org. Chem.*, vol. 63, No. 26, 1998, pp. 10063-10068.

V. K. Pandey, "3, 6-Dibenzoyl-1, 4-Bis (5'-Alkoxy-1', 3', 4' Thiadiazolyl)-1, 2-Di-Hydrol-1, . . . ", *Indian Drugs*, vol. 23, 1986, pp. 500-504.

V. K. Pandey et al, "Studies on 3, 6-Dibenzoyl-1, 4-Di-[2'-(5'-Alkyl-1',3',4'-Thiadiazolyl]. . . ", *Indian Journal of Pharmaceutical Sciences*, vol. 44, Nov.-Dec. 1982, pp. 155-157.

* cited by examiner

CANNABIMIMETIC LIGANDS

This application is the National Stage of International Application No. PCT/US02/02157, filed Jan. 25, 2002, which claims the benefit of U.S. Provisional Application No. 60/264,385, filed Jan. 26, 2001, the contents of each of which are incorporated herein by reference in their entirety.

FIELD OF THE INVENTION

The present invention relates generally to compounds exhibiting cannabimimetic activity and is more particularly concerned with new and improved cannabimimetic compounds exhibiting preferentially high binding affinities for the CB2 cannabinoid receptor, methods of preparation of such compounds, pharmaceutical preparations employing these compounds and methods of administering therapeutically effective amounts of these compounds to provide a physiological effect.

BACKGROUND OF THE INVENTION

Classical cannabinoids such as the marijuana derived cannabinoid. $^9$-tetrahydrocannabinol, ($^9$-THC) produce their pharmacological effects through interaction with specific cannabinoid receptors in the body. So far, two cannabinoid receptors have been characterized: CB1, a central receptor found in the mammalian brain and peripheral tissues and CB2, a peripheral receptor found only in the peripheral tissues. Compounds that are agonists or antagonists for one or both of these receptors have been shown to provide a variety of pharmacological effects.

There is considerable interest in developing new cannabimimetic compounds possessing preferentially high affinity for the CB2 receptor. Such compounds that preferentially stimulate the CB2 receptor, directly or indirectly, can provide clinically useful effects without major effects on the subject's central nervous system and can offer a rational therapeutic approach to a variety of disease states.

SUMMARY OF THE INVENTION

It has now been found that certain chemical compounds surprisingly possess cannabimimetic properties. Broadly, in one aspect of the invention the novel cannabimimetic compounds can be represented by the structural Formula I, physiologically acceptable salts, diasteromers, enantiomers, double bond isomers or mixtures thereof.

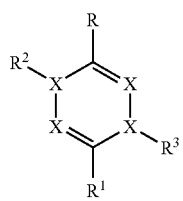

Formula I wherein:
R comprises $C_{1-6}$alkoxy; N-alkyl; S-alkyl; $C_{1-3}$haloalkoxy; $C_{1-6}$alkylketo; $C_{1-6}$alkylthioketo; $CO_2H$; $CONR^6R^7$ where $R^6$ and $R^7$ each independently comprise H, lower alkyl and carbalkoxyloweralkyl; ester; thioester; reversed ester; reversed thioester; reversed amide or

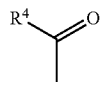

wherein $R^4$ comprises methoxy, ethoxy, propoxy, methyl, amino, methylamino, ethylamino, butylamino,

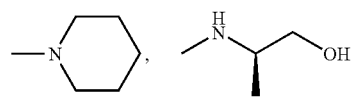

or an enantiomer thereof, or

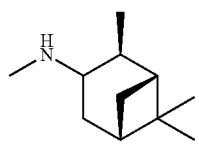

or an enantiomer thereof;
$R^1$ comprises $C_{1-6}$alkoxy; N-alkyl; S-alkyl; $C_{1-3}$haloalkoxy; $C_{1-6}$alkylketo; $C_{1-6}$alkylthioketo; $CO_2H$; $CONR^6R^7$ where $R^6$ and $R^7$ each independently comprise H, lower alkyl and carbalkoxyloweralkyl; ester; thioester; reversed ester; reversed thioester; reversed amide; or

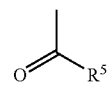

wherein $R^5$ comprises methoxy, ethoxy, propoxy, methyl, amino, methylamino, ethylamino, butylamino,

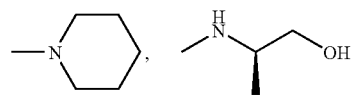

or an enantiomer thereof, or

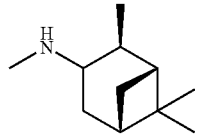

or an enantiomer thereof;
$R^2$ and $R^3$ each independently comprise phenyl; benzyl; α-naphthyl; methylene-α-naphthyl; β-naphthyl; methylene-β-naphthyl; 5 or 6 membered heteroaromatic rings comprising 1 to 3 heteroatoms each independently selected from N, O, and S, provided that no more than 1 heteroatom is O or S; methylene-5 or 6 membered heteroaromatic rings comprising 1 to 3 heteroatoms each independently selected from N, O, and S, provided that no more than 1 heteroatom is O or S; any of the above comprising up to 3 substituents independently selected from halo, hydroxyl, amino, lower alkyl amino, $C_{1-6}$alkyl, $C_{1-6}$alkoxy, $C_{1-6}$alkylthio, CN, $CF_3$, $CO_2H$, $CONR^6R^7$ where $R^6$ and $R^7$ each independently comprise H, lower alkyl or carbalkoxyloweralkyl, $SO_3H$, and $SO_2NR^6R^7$ where $R^6$ and $R^7$ each independently comprise H, lower alkyl or carbalkoxyloweralkyl; terpenes; $C_{1-10}$alkyl; 1,1-dimethyl alkyl or alkoxy; and each X independently comprises CH or N to yield either carbocyclic rings or heterocyclic rings. It should be understood that when each X is CH, the, invention in any aspect encompasses the corresponding benzene derivatives i.e. 1,4-dihydrobenzenes.

In another aspect of the invention a preferred novel cannabimimetic compound can be represented by structural Formula II,

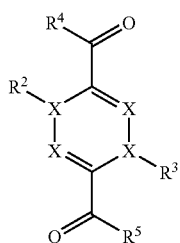

Formula II wherein:

X comprises N;

$R^4$ and $R^5$ each independently comprise methoxy, ethoxy, propoxy, methyl, amino, methylamino, ethylamino, butylamino,

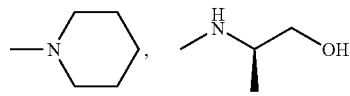

or an enantiomer thereof, or

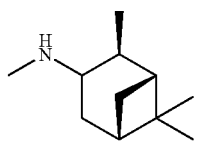

or an enantiomer thereof; and $R^2$ and $R^3$ each comprise phenyl.

In another aspect of the invention a preferred novel cannabimimetic compound can be represented by structural Formula II wherein:

X comprises N;

$R^4$ comprises ethoxy;

$R^5$ comprises methyl,

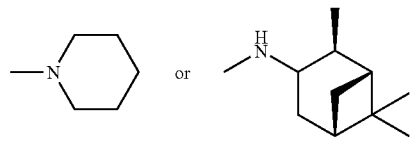

or an enantiomer thereof; and $R^2$ and $R^3$ each comprise phenyl.

In another aspect of the invention a preferred novel cannabimimetic compound can be represented by structural Formula II wherein:

X comprises N;

$R^4$ and $R^5$ each comprise ethoxy; and $R^2$ and $R^3$ each independently comprise p-NO2 substituted phenyl, p-Cl substituted phenyl, p-Br substituted phenyl, p-OMe substituted phenyl, o, p-dichloro substituted phenyl, 1-napthyl or phenyl ketone.

In another aspect of the invention a preferred novel cannabimimetic compound can be represented by structural Formula II wherein:

X comprises N;

$R^4$ and $R^5$ each comprise ethoxy;

$R^2$ comprises phenyl; and $R^3$ comprises p-Cl substituted phenyl or 1-napthyl.

In another aspect of the invention a preferred novel cannabimimetic compound can be represented by structural Formula II wherein:

X comprises N;

$R^4$ and $R^5$ each comprise ethoxy;

$R^2$ comprises p-Br substituted phenyl; and $R^3$ comprises p-Cl substituted phenyl.

In another aspect of the invention a preferred novel cannabimimetic compound can be represented by structural Formula II wherein:

X comprises CH;

$R^4$ and $R^5$ each comprise ethoxy; and $R^2$ and $R^3$ each comprise phenyl.

In another aspect of the invention a preferred novel cannabimimetic compound can be represented by structural Formula II wherein:

X comprises N;

$R^4$ and $R^5$ each comprise ethoxy; and $R^2$ and $R^3$ each comprise napthyl.

Naturally, the invention in any aspect also encompasses any of physiologically acceptable salts, diasteromers, enantiomers, double bond isomers and mixtures of the above inventive compounds. Further, when each X is CH, the invention in any aspect encompasses the corresponding benzene derivatives i.e. 1,4-dihydrobenzenes. The compounds represented by structural Formula II are also encompassed within the broader invention represented by structural Formula I.

Unless otherwise specifically defined, "alkyl" refers to a linear, branched or cyclic alkyl group having from 1 to about 9 carbon atoms including, for example, methyl, ethyl, propyl, butyl, hexyl, octyl, isopropyl, isobutyl, tert-butyl, cyclopropyl, cyclohexyl, cyclooctyl, vinyl and allyl. The alkyl group can be saturated or unsaturated and substituted or unsubstituted. Unless otherwise specifically defined, "lower-alcohol" refers to the general formula alkyl-OH. Unless otherwise specifically defined, "alkoxy" refers to the general formula —O-alkyl. Unless otherwise specifically defined, "alkylmercapto" refers to the general formula —S-alkyl.

Unless otherwise specifically defined, 'alkylamino' refers to the general formula —(NH)-alkyl. Unless otherwise specifically defined, "di-alkylamino" refers to the general formula —N-(alkyl)$_2$. Unless otherwise specifically defined, an aromatic ring is an unsaturated ring structure, substituted or unsubstituted, that includes only carbon as ring atoms. Unless otherwise specifically defined, a heteroaromatic ring is an unsaturated ring structure, substituted or unsubstituted, that has carbon atoms and one or more heteroatoms, including oxygen, nitrogen and/or sulfur, as ring atoms, for example, pyridine, furan, quinoline, and their derivatives. Unless otherwise specifically defined, a carbocyclic ring is a saturated ring structure, substituted or unsubstituted, that includes only carbon as ring atoms, for example, cyclohexane. Unless otherwise specifically defined, a heterocyclic ring is a saturated ring structure, substituted or unsubstituted, that has carbon atoms and one or more heteroatoms, including oxygen, nitrogen and/or sulfur, as ring atoms, for example, piperidine, morpholine, piperazine, and their derivatives. Unless otherwise specifically defined, a terpene is an unsaturated hydrocarbon having the general formula $C_{10}H_{16}$ and based on the isoprene ($C_6H_8$) unit. As used herein a terpene may be acyclic, monocyclic or polycyclic and substituted or unsubstituted.

Substituent groups for the above moieties useful in the invention are those groups that do not significantly diminish the biological activity of the inventive compound. Unless otherwise specifically defined, substituent groups that do not significantly diminish the biological activity of the inventive compound include, for example, —OH, —NH$_2$, alkoxy, halogen, —CF$_3$, —CN, —NCS, azido, —CONH, —NHCO, sulfonamide, lower alcohol.

Some of the inventive cannabinoid compounds exhibit high affinity for the CB2 cannabinoid receptor. Thus, another aspect of the invention is use of at least one of the inventive compounds to interact with the CB2 cannabinoid receptor.

Further, some of the inventive cannabinoid compounds show a surprisingly higher selectivity for the CB2 cannabinoid receptor. These inventive selective compounds are able to interact with the CB2 cannabinoid receptor, without affecting the CB1 cannabinoid receptor to the same degree. Therefore, still another aspect of the invention is use of at least one of the inventive compounds to preferentially interact with the CB2 cannabinoid receptor.

Some of the inventive cannabinoid compounds can act as high affinity modulators for the CB2 cannabinoid receptor. The inventive cannabinoid compounds therefore are potential therapeutic agents through the modulation of the CB2 cannabinoid receptor.

Some of the novel cannabinoid compounds described herein may be agonists for the CB2 cannabinoid receptor. The inventive cannabinoid agonists interact with the CB2 cannabinoid receptor binding site to initiate a physiological or a pharmacological response characteristic of that receptor. Therefore, a further aspect of the invention is use of at least one of the inventive compounds to initiate an agonistic response from a CB2 cannabinoid receptor.

The inventive cannabinoid compounds described herein, and physiologically acceptable salts thereof, have pharmacological properties when administered in therapeutically effective amounts for providing a physiological response in individuals and/or animals. Thus, another aspect of the invention is the administration of a therapeutically effective amount of at least one of the inventive cannabimimetic compounds, or a physiologically acceptable salt thereof, to an individual or animal to provide a physiological response.

The inventive cannabinoid compounds have uniquely short and simple synthesis routes. Thus another aspect of the invention are methods of preparation of the inventive cannabinoid compounds.

A better understanding of the invention will be obtained from the following detailed description of the article and the desired features, properties, characteristics, and the relation of the elements as well as the process steps, one with respect to each of the others, as set forth and exemplified in the description and illustrative embodiments.

DESCRIPTION OF A PREFERRED EMBODIMENT

As used herein a "therapeutically effective amount" of a compound, is the quantity of a compound which, when administered to an individual or animal, results in a sufficiently high level of that compound in the individual or animal to cause a discernible increase or decrease in stimulation of cannabinoid receptors. The discernible increase or decrease in stimulation of cannabinoid receptors provides a physiological response in the individual or animal. The inventive compounds described herein, and physiologically acceptable salts thereof, have pharmacological properties when administered in therapeutically effective amounts for providing a physiological response useful to: treat pain, peripheral pain, glaucoma, epilepsy and nausea such as associated with cancer chemotherapy; cancer, especially glioma and breast cancer; neurodegenerative diseases including Multiple Sclerosis, Parkinson's Disease, Huntington's Chorea and Alzheimer's Disease, reduce fertility; prevent or reduce diseases associated with motor function such as Tourette's syndrome; prevent or reduce inflammation; provide neuroprotection; to modulation of the immune system; or treat a combination of the above. Typically, a "therapeutically effective amount" of the novel cannabimimetic compounds may range from about 10 mg/day to about 1,000 mg/day.

As used herein, an "individual" refers to a human. An "animal." refers to, for example, veterinary animals, such as dogs, cats, horses and the like, and farm animals, such as cows, pigs and the like.

The compound of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically to acceptable vehicles may include, for example, saline, sterile water, Ringer's solution, and isotonic sodium chloride solutions. The specific dosage level of compound will depend upon a number of factors, including, for example, biological activity of the particular preparation, age, body weight, sex and general health of the individual being treated.

The following examples are given for purposes of illustration only in order that the present invention may be more fully understood. These examples are not intended to limit in any way the scope of the invention unless otherwise specifically indicated.

EXAMPLES

TABLE 1 illustrates some cannabinoids of the present invention (compounds 1-25).

TABLE 1

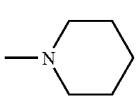

| compound | X | $R^4$ | $R^5$ | $R^2$ | $R^3$ | Selectivity for CB2 | Ki(nM) CB1 | Ki(nM) CB2 |
|---|---|---|---|---|---|---|---|---|
| 1 | N | $OCH_3$ | $OCH_3$ | phenyl | phenyl | 81 | $3.1 \times 10^4$ | 381 |
| 2 | N | $OC_2H_5$ | $OC_2H_5$ | phenyl | phenyl | 88 | 1672 | 19 |
| 3 | N | $OC_3H_7$ | $OC_3H_7$ | phenyl | phenyl | 27 | 618 | 23.3 |
| 4 | N | $CH_3$ | $CH_3$ | phenyl | phenyl | 1 | $1.0 \times 10^4$ | $1.0 \times 10^4$ |
| 5 | N | $NH_2$ | $NH_2$ | phenyl | phenyl | 1 | $1.0 \times 10^4$ | $1.0 \times 10^4$ |
| 6 | N | $NHCH_3$ | $NHCH_3$ | phenyl | phenyl | 1 | $6.6 \times 10^4$ | $1.0 \times 10^5$ |
| 7 | N | $NHC_2H_5$ | $NHC_2H_5$ | phenyl | phenyl | 1 | $1.0 \times 10^5$ | $1.0 \times 10^5$ |
| 8 | N | $NHC_4H_9$ | $NHC_4H_9$ | phenyl | phenyl | 23 | $1.6 \times 10^4$ | 692 |
| 9 | N | 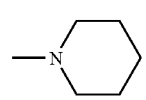 | 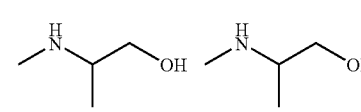 | phenyl | phenyl | 42 | 9985 | 221 |
| 10 | N | 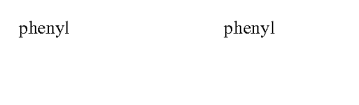 | 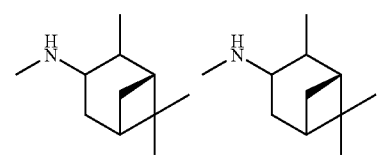 | phenyl | phenyl | 1 | $1.0 \times 10^5$ | $1.0 \times 10^5$ |
| 11 | N | 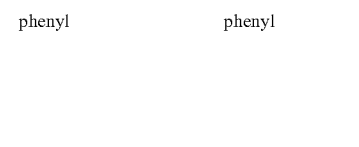 | 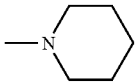 | phenyl | phenyl | 1 | $1.0 \times 10^5$ | $1.0 \times 10^5$ |
| 12 | N | $CH_3$ | $OC_2H_5$ | phenyl | phenyl | 24 | 7704 | 327 |
| 13 | N | 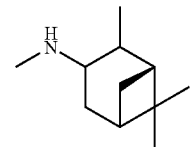 | $OC_2H_5$ | phenyl | phenyl | 20 | 5044 | 255 |
| 14 | N | 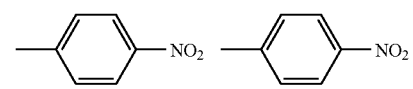 | $OC_2H_5$ | phenyl | phenyl | 2.6 | 2054 | 805 |
| 15 | N | $OC_2H_5$ | $OC_2H_5$ | 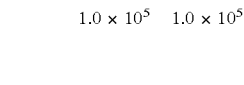 | 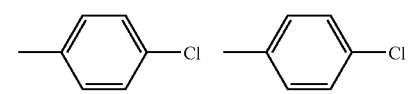 | | $1.0 \times 10^5$ | $1.0 \times 10^5$ |
| 16 | N | $OC_2H_5$ | $OC_2H_5$ |  | | 4.3 | 208 | 48 |

TABLE 1-continued

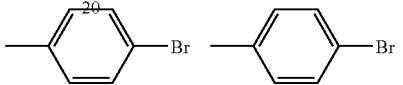

| compound | X | R⁴ | R⁵ | R² | R³ | Selectivity for CB2 | Ki(nM) CB1 | Ki(nM) CB2 |
|---|---|---|---|---|---|---|---|---|
| 17 | N | OC$_2$H$_5$ | OC$_2$H$_5$ | 4-Br-C$_6$H$_4$ | 4-Br-C$_6$H$_4$ | 3.5 | 350 | 200 |
| 18 | N | OC$_2$H$_5$ | OC$_2$H$_5$ | 4-OMe-C$_6$H$_4$ | 4-OMe-C$_6$H$_4$ | 64 | 4585 | 72 |
| 19 | N | OC$_2$H$_5$ | OC$_2$H$_5$ | 2,4-Cl$_2$-C$_6$H$_3$ | 2,4-Cl$_2$-C$_6$H$_3$ | 1 | 1.0 × 10$^4$ | 1.0 × 10$^4$ |
| 20 | N | OC$_2$H$_5$ | OC$_2$H$_5$ | 1-naphthyl | 1-naphthyl | 524 | 1.0 × 10$^6$ | 1906 |
| 21 | N | OC$_2$H$_5$ | OC$_2$H$_5$ | PhC(O)- | PhC(O)- | 1 | 1.0 × 10$^5$ | 1.0 × 10$^5$ |
| 22 | N | OC$_2$H$_5$ | OC$_2$H$_5$ | 4-Cl-C$_6$H$_4$ | C$_6$H$_5$ | 34 | 1500 | 43 |
| 23 | N | OC$_2$H$_5$ | OC$_2$H$_5$ | 4-Cl-C$_6$H$_4$ | 4-Br-C$_6$H$_4$ | 18 | 542 | 30 |
| 24 | N | OC$_2$H$_5$ | OC$_2$H$_5$ | 1-naphthyl | C$_6$H$_5$ | 40 | 7357 | 182 |
| 25 | C | OC$_2$H$_5$ | OC$_2$H$_5$ | C$_6$H$_5$ | C$_6$H$_5$ | 1.6 | 1203 | 747 |

Preparation of Compounds:
The materials listed in Table 1 can be prepared by following one of the methods outlined in Scheme 1.
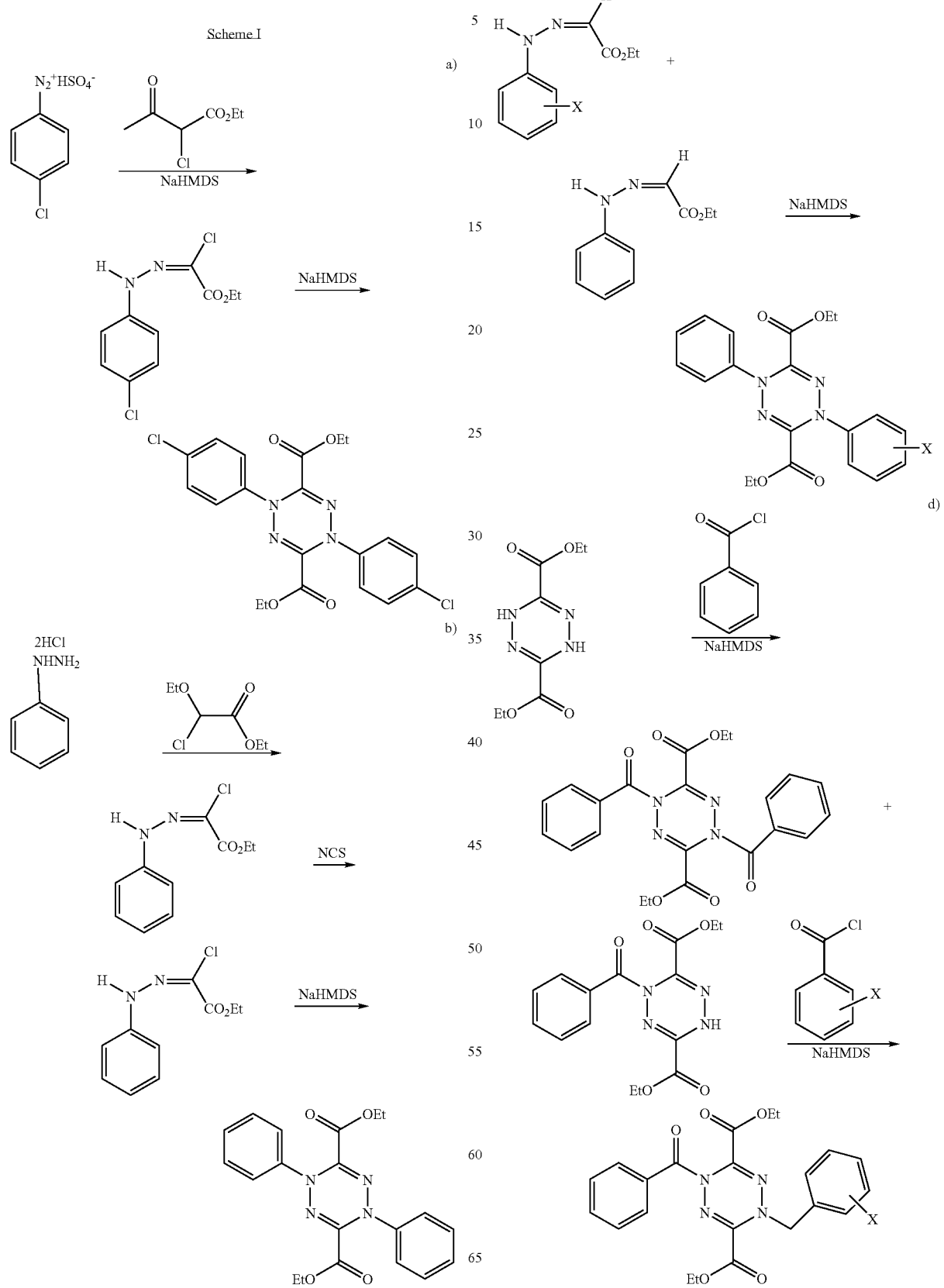

It has been found preferable to carry out the reactions involving sodium hexamethyldisilazane at temperatures in the range of about 25° C. to about −78° C.

It should be noted that conversion of esters of the invention to their corresponding methyl ketones can be accomplished using the method of M. Girardot, R. Nomak, and J. K. Snyder; J. Org. Chem. (1998) 63(26) 10063-10068, the content of which is incorporated by reference herein. Such conversion is within the scope of the present invention.

Examples of specific analogs were prepared as follows:

Ethyl Phenylhydrizinochloromethylenecarboxylate (5.6)

Method A: Concentrated sulfuric acid (50 mL, 96%) was slowly dropped into a solution of aniline (30 g. 0.32 mol) ill ethanol (280 mL) until the white precipitate newly formed disappeared again at 0-5° C. To this mixture, isoamylnitrite (40 g, 0.34 mol) was slowly added with stirring. An equal volume of ethyl ether was added to precipitate the product. The mixture was filtered and the residue washed with ethanol:ether (1:1, v/v) to provide a crude greenish solid of benzenediazonium sulfuric acid salt for the following reaction.

Mixed with a small amount of ice water, the above product was added to a mixture of ethyl α-chloroacetoacetate (72.6 g, 0.44 mol), ethanol (616 mL), and sodium acetate (54.12 g, 0.66 mol) in several portions at 0 to about 5° C. After stirring for 3 h, the reaction mixture was poured into a large volume of water and left overnight. Collecting the precipitate by filtration provided a light brown solid 5.6 (21.72 g, overall yield 30%) with high purity. Recrystallization was performed from ethanol to give crystal-like solid with mp 77-78° C. [lit (Bowack and Lapworth, 1905) 71-72° C.]. $^1$H NMR (200 MHz, CDCl$_3$) δ (ppm): 1.43 (t, J=7.4 Hz, 3H), 4.39 (q, J=7.4 Hz, 2H), 7.02-7.08 (m, $^1$H), 7.20-7.38 (m, 4H), 8.34 (b, 1H). GC-MS (EI): 226 (M+), 181 (M+— OCH$_2$CH$_3$), 152, 91, 65.

Method B: To a solution of ethyl phenylhydrazono acetic acid ester (5.25), 172 mg, 0.88 mmol) in ethyl acetate (5 mL) was added N-chlorosuccinimide (CNS, 129.7 mg, 1.1 mmol), and the resulting reaction mixture was heated at 60-70° C. for 24 h. TLC indicated the reaction was complete. After removal of the solvent, the crude product was subjected to silica gel column chromatography with petroleum ether and ethyl acetate (20:1) as eluent system to afford the title compound in 83.3% yield.

Ethyl naphthalenylhydrizinochloromethylenecarboxylate (5.7)

Analogously to the synthesis of 5.6, the 1-naphthalenediazonium sulfuric acid salt was first prepared and then reacted with ethyl 2-chloro acetoacetate to provide the title compound in 16.6% overall yield as red-brown solid, mp 83-84° C. (recrystallization from ethyl acetate-petroleum ether). $^1$H NMR (200 MHz, CDCl$_3$) δ (ppm): 1.43 (t, J=7.1 Hz, 3H), 4.43 (q, J=7.1 Hz, 2H), 7.48-7.65 (m, 5H), 7.86-7.90 (m, 2H), 8.94 (s, 1H). $^{13}$C NMR δ ppm: 14.46, 63.10, 111.49, 118.16, 119.26, 122.78, 123.56, 126.41, 129.15, and 134.35, 137.10, 159.3.

Ethyl 4-chlorophenylhydrizinochloromethylenecarboxylate (5.12)

Using 4-chlorobenzenediazonium hexafluorophosphate as starting material and a method analogous to the synthesis of 5.6, the title compound was prepared in 61% yield as a yellow solid, mp 146-1470° C. $^1$H NMR (200 MHz, CDCl$_3$) δ (ppm): 8.30 (s, 1H), 7.21 (d, J=8.0 Hz, 2H), 4.40 (dd, J=7.0 Hz, 2H), 1.39 (t, J=7.0 Hz, 3H). GC-MS (EI), m/e: 261 (M+), 186, 125, 99.

Ethyl 4-bromophenylhydrizinochloromethylenecarboxylate (5.13)

Using 4-brombenezenediazonium tetrafluoroborate as starting material, and a method analogous to the synthesis of 5.6, the title compound was prepared in 61% yield as yellow solid, mp 160-161° C. $^1$H NMR (200 MHz, CDCl$_3$ δ (ppm): 1.40 J (t, J=7.2 Hz, 3H), 4.39 (dd. J=; 7.1 Hz, 2H), 7.11 (d, J=8.6 Hz, 2H), 7.44 (d, J=8.6 Hz, 2H), 8.30 (s, 1H). GC-MS (EI), no GC peak.

Ethyl 4-nitrophenylhydrizinochloromethylenecarboxylate (5.15)

Using 4-nitrobenzenediazonium hexafluorophosphate and ethyl 2-chloroacetoacetate as starting materials, and a method analogous to the synthesis of 5.6, the title compound was prepared in 70% yield as yellow solid, mp 193-194° C. $^1$H NMR (200 MHz, CDCl$_3$) δ (ppm): 1.43 (t, J=7.2 Hz, 3H), 4.42 (q, J=7.2 Hz, 2H), 732 (d, J=7.3 Hz. 2H), 8.25 (d, J=8.8 Hz, 2H), 8.57 (b, 1H). GC-MS (EI): no GC peak.

Acetyl phenylhydrizinochloromethylene (5.18)

Using benzenediazonium salt as starting material reaction with 3-chloro-2,4-pentanedione (5.17) in a method analogous to the synthesis of 5-6 provided the title compound in 14% yield as brown solid, mp 129.5-130° C. $^1$H NMR (200 MHz, CDCl$_3$) δ (ppm): 8.48 (s, 1H), 7.31 (dd, J=8.5 Hz, 4H), 7.10 (t, J=8.0 Hz, 1H), 2.50 (s, 3H). GC-MS (EI), m/e: 196(M+), 118, 91, 77, 65.

Acetyl 4-chlorophenylhydrizinochloromethylene (5.19)

Using 4-chlorobenzene-diazonium hexafluorophosphate as starting material, and reacting with 3-chloro-2,4-pentanedione (5.17) analogously to the synthesis of 5-6 provided the title compound in 92% yield as red-brown solid, mp 161-162° C. $^1$H NMR (200 MHz, CDCl$_3$) δ (ppm): 8.45 (s, 1H), 7.31 (dd, J=8.5 Hz, 4H), 2.57 (s, 3H). GC-MS (EI), m/e: 231(M+) 194, 179, 152. 125, 99.

Ethyl phenylhydrazono acetic acid ester (5.25)

Phenyl hydrazine hydrochloride (1.45 g, 10 mmol) was suspended in water (5 mL) (the resulting mixture showed pH −4). To this mixture was added a solution of 2-chloro-2-ethoxyacetate (prepared from ethyl 2,2-diethoxyacetate and acetyl chloride without further purification) in dioxane (12.5 mL) in small portions while cooling with tap water. After: 3 h, the reaction mixture was neutralized to pH-8 with sodium hydroxide solution and evaporated under vacuum to half its volume. Water was added to the mixture and the resulting emulsion was extracted with dichloromethane. The organic layers were separated, dried over $MgSO_4$, filtered, and evaporated in vacuo. The crude product was subjected to recrystallization from ethyl acetate and petroleum ether to afford the title compound 5.25 as light brown solid (200 mg, 10.4%), mp 129-131° C. (lit: 130-132° C., Jung, et al, 1982). $^1$H NMR (200 MHz, $CDCl_3$), δ 1.36 (t. J=7.1 Hz, 3H), 4.32 (q, J=7.1 Hz. 2H), 5.30 (s, 1H). 6.96-7.35 (m, 5H), 8.33 (b, 1H).

1,4-Di-(4-chlorophenyl)-1,4-dihydro-1,2,4,5-tetrazine-3,6-dicarboxylic acid diethyl ester (5.28)

To a stirring solution of 5.12 (100 mg, 0.38 mmol) in THF was added sodiohexamethyldisilazane (0.38 mL, 1 M solution in THF) at 0° C. The reaction mixture was warmed up to RT and stirred for another 3 h. Work-up with ammonium chloride aqueous solution and extraction with ethyl acetate, which was dried over sodium sulfate provided the crude product after removal of the solvent under vacuum. The crude product was purified by flash column chromatography to afford the title compound (31.5 mg, 37%) as an orange solid. $^1$H NMR (200 MHz, $CDCl_3$) δ 7.28 (dd, J=8.5 Hz, 8H), 4.18 (dd, J=7.0 Hz, 4H). 1.10 (t, J=7.0 Hz, 6H). $^{13}$C NMR (200 MHz, $CDCl_3$) δ 159.2, 141.5. 140.2, 131.0, 129.4. 120.2, 63.3. 13.8. GC-MS (EI), m/e: 449(M+), 376, 152, 111. Anal. ($C_{20}H_{18}Cl_2N_4O_4$) C, H, N.

1,4-Di-(α-naphthalene)-1,4-dihydro-1,2,4,5-tetrazine-3,6-dicarboxylic acid diethyl ester (5.32)

Analogously to the synthesis of compound 5.28, except that the reaction was run at −78° C. after failure at 0° C., the title compound was prepared from 5.7 in 61% yield as a red brown solid, mp 129-130° C. recrystallization from ethyl acetate). $^1$H NMR (200 MHz, $CDCl_3$) δ 0.66 (t, J=7.0 Hz, 6H). 3.82 (q, J=7.0 Hz, 4H); 7.46-7.53 (m. 4H), 7.59 (d, J=7.2 Hz, 2H), 7.78 (d, J=8.0 Hz, 2H), 7.85-7.90 (m, 4H), 8.07-8.12 (m. 2H). Anal. ($C_{28}H_{24}N_4O_4$) C, H, N.

1,4-Diphenyl-1,4-dihydro-3,6-diacetyl-1,2,4,5-tetrazine (5.33)

Analogously to the synthesis of compound 5.28, the title compound was prepared from 5.17 in 31% yield. $^1$H NMR (200 MHz, $CDCl_3$) δ 7.30 (dd, J=8.5 Hz. 8H), 7.10 (t, J=8.0 Hz, 2H), 2.50 (s, 6H). GC-MS (EI), m/e. 320(M+), 278, 207, 91, 77.

1,4-Di-(4-chlorophenyl)-1,4-dihydro-3,6-diacetyl-1,2,4,5-tetrazine (5.34)

Analogously to the synthesis of compound 5.28, the title compound was prepared from 5.18 in 20% yield. $^1$H NMR (200 MHz, $CDCl_3$) δ 7.28 (dd, J=8.5 Hz, 8H), 2.49 (s, 6H). GC-MS (EI), m/e: 346 ($M^+$ —$COCH_3$, 304.

Dimethyl 1,4-diphenyl-1,4-dihydro-1,2,4,5-tetrazine-3,6-dicarboxylate (5.37)

Sodium cyanide (0.5 mg) was added to a solution of compound 5.1 (38 mg, 0.1 mmol) in methanol (0.5 mL) and the resulting suspension was stirred at room temperature for 12 h. After removal of solvent, the residue was dissolved in dichloromethane and washed with water. The organic layer was dried over sodium sulfate and evaporated under vacuum to provide the title compound 5.37 (35 mg, 99%) as an orange solid. Recrystallization from 10% dichloromethane in ethanol afforded the title compound as an orange solid, mp 171-172° C. $^1$H NMR (200 MHz, $CDCl_3$) δ 7.41-7.09 (m. 10H), 3.69 (s, 6H). $^{13}$C NMR (200 MHz, $CDCl_3$) δ 160.0, 141.5, 129.3, 125.6, 118.7, and 53.5. Anal. ($C_{18}H_{16}N_4O_4$) C, H, N.

Dipropyl-1,4-diphenyl-1,4-dihydro-1, 2, 4, 5-tetrazine-3,6-dicarboxylate (5.38)

The title compound was prepared in n-propanol analogously to the synthesis of 5.37 in 98% yield as an orange solid, mp 82.5-83° C. $^1$H NMR (200 MHz. $CDCl_3$) O 7.30 (m, 10H). 4.02 (q, J=6.0 Hz. 4H), 1.44 (t, J=7.2 Hz, 4H), 0.75 (t, J=7.2 Hz, 6H). $^{13}$C NMR (200 MHz, $CDCl_3$) δ 159.8, 141.9, 141.7, 129.3, 125.5, 118.6, 68.6, 21.7, and 10.3. GC-MS (EI). m/e: 408 (M+), 322, 118, and 77. Anal. ($C_{22}H_{24}N_4O_4$) C, H, N.

1,4-Diphenyl-1,4-dihydro-1,2,4,5-tetrazine-3,6-dicarboxylic amide (5.39)

Liquid ammonia was slowly added to a suspension of 5.1 (76 mg, 0.2 mmol) and sodium cyanide (1 mg, 0.02 mmol) in methanol (2 mL) in a sealing tube at −60 to about −80° C. for 2 min. After slow warming up to −20° C., the reaction mixture was sealed, and warmed up to room temperature. After stirring at RT for two days, the reaction mixture was cooled down to −20° C. again for opening the seal, and then warmed up to RT for workup. The solvent was removed by rotary evaporation, and the residue was dissolved in ethanol for filtration. After concentration, the filtrate gave the crude product, which was recrystallized from ethanol to provide the title compound 5.39 as a red-brown solid (18 mg, 28%). The mother liquor afforded another portion of the title compound (40 mg, 62%) after concentration and flash column purification. The overall yield is 90%, mp 241-242° C. $^1$H NMR (200 MHz, $CDCl_3$) δ 8.43 (s, 2H), 7.95 (s, 2H), 7.28 (m, 8H), 7.08 (t, J=5.6 Hz. 2H). $^{13}$C NMR (200 MHz, $CDCl_3$) δ 160.3, 144.4, 141.3, 128.6. 124.1, and 117.8. Anal. ($C_{16}H_{14}N_6O_2$) C, H, N.

N,N-Dimethyl-1,4-diphenyl-1,4-dihydro-1,2,4,5-tetrazine-3,6-dicarboxylic di-amide (5.40)

Using methyl amine (2 M solution of methyl amine in methanol) as reactant, the title compound was prepared analogously to the synthesis of compound 5.37 in 99% yield (the reaction was finished in 4 hours) as an orange solid, mp 243-243.5° C. $^1$H NMR (200 MHz, $CDCl_3$) δ 7.30 (m, 10H), 6.60 (m, 2H), 2.83 (s. 3H), 2.81 (s, 3H), $^{13}$C NMR (200 MHz, $CDCl_3$) δ 159.2, 143.8, 141.8, 128.9. 125.5, 119.6, 113.0, and 26.7. Anal. ($C_{18}H_{18}N_6O_2$) C, H, N.

N,N-Diethyl-1,4-diphenyl-1,4-dihydro-1,2,4,5-tetrazine-3,6-dicarboxylic di-amide (5.41)

Using ethylamine (2M solution of ethyl amine in methanol) as reactant, the title compound was prepared analogously to the synthesis of compound 5.41 in 100% yield as an orange solid, mp 239-240° C. $^1$H NMR (200 MHz, $CDCl_3$) δ 7.40-7.13 (m, 10H), 6-53 (b, 2H), 3.28 (m, 4H), 1.13 (t, J=7.4 Hz, 6H). $^{13}$C NMR (200 MHz, $CDCl_3$) δ 158.1, 144.0, 141.9, 128.9, 125.4, 119.6, 115-6, 114.6, 35.1, and 14.7. Anal. ($C_{20}H_{22}N_6O_2$) C, H, N.

N,N-Dibutyl-1,4-diphenyl-1,4-dihydro-1,2,4,5-tetrazine-3,6-dicarboxylic di-amide (5.42)

Using butyl amine as reactant, the title compound was prepared analogously to the synthesis of compound 5.41 in 92% yield as an orange solid, mp 160-161° C. $^1$H NMR (200 MHz, CDCl$_3$) δ 7-39-7.13 (m, 10H). 6.55 (m. 2H). 3.26 (m, 4H), 2.15-1.23 (m, 8H), 0.91 (t, J=7.2 Hz, 6H). $^{13}$C NMR (200 MHz, CDCl$_3$) δ 158.2, 144.0, 141.87 128.9, 125.4, 119.4, 39.8, 31.5, 20.1, and 13.8. Anal. ($C_{24}H_{30}N_6O_2$) C, H, N.

N,N-Di[β-hydroxyl-α-(R)-methyl]ethyl-1,4-diphenyl-1,4-dihydro-1,2,4,5-tetrazine-3,6-dicarboxylic di-amide (5.43)

Using D-alainol as reactant, the title compound 5.43 was prepared analogously to the synthesis of compound 5.41 in 94% yield as an orange solid (the product was purified by flash column chromatography with 4% ethanol-dichloromethane as eluent), mp 191-191.5° C. $^1$H NMR (200 MHz, CDCl$_3$) δ 7.40-7.15 (m, 10H), 6.73 (d, J=7.8 Hz, 2H), 4.02-3.94 (m, 2H), 3.64-3.59 (m, 2H), 3.50-3.42 (m, 2H), 2.2 (m, 2H), 1.12 (d, J=6.2 Hz, 6H). $^{13}$C NMR (200 MHz, DMSO) δ 158.2, 144.7, 141.2, 128.6, 124.3, 118.4, 63;7, 47.3, and 16.4. Anal. ($C_{22}H_{26}N_6O_4$) C, H, N.

N,N-Diisopinocampheyl-1,4-diphenyl-1,4-dihydro-1,2,4,5-tetrazine-3,6-dicarboxylic di-amide (5.44) and 1,4-Diphenyl-1,4-dihydro-1,2,4,5-tetrazine-3-carboxylic N-isopinocampheyl amide-6-carboxylic ethyl ester (5.57)

A solution of isopinocampheylamine (153 mg, 1 mmol) and LiHMDS (1.2 mL, 1.0 M solution in THF) in THF was stirred for 30 min at −60° C. Compound 5.1 (76 mg, 0.2 mmol) in THF (1 mL) was added dropwise, followed by stirring for another 10 h at the same temperature. After warming up to RT, the reaction was terminated by addition of water followed by ammonium chloride aqueous solution. Extracted with ethyl acetate, the organic layer was dried over sodium sulfate, filtered, and evaporated to provide the crude product. Purification on a flash column (petroleum ether:ethyl acetate 3%-10%, v/v) afforded the title compound 5.44 (60 mg, 50.4%) and 5.57 (28.5 mg, 29.3%). For; compound 5.44: mp 262-263° C. $^1$H NMR (500 MHz; DMSO:CDCl$_3$=2:1, v/v), δ (ppm): 9.03 (d, J=8.6 Hz, 2H, NH), 7.35-730 (m, 8H), 7.14-7.11 (b, 2H), 4.03 (b, 2H), 2.31-2.26 (b, 4H), 1.96-1.89 (b, 4H), 1-75 (b, 2H). 1.57 (b, 2H), 1.19 (s, 6H), 1.08 (d, J=9.4 Hz, 2H), 0.96 (s, 6H), 0.92 (d, J=7.2 Hz, 6H). $^{13}$C NMR (200 MHz, DMSO:CDCl$_3$=2:1, v/v). δ 158.2J 145.1, 141.3, 128.5, 124.3J 118.5. 47.4, 47.2, 43.7, 35.1, 33.7, 27.8, 23.0, and 20.5. Anal. ($C_{36}H_{46}N_6O_2$) C, H, N. For compound 5.57, mp 157.5-158.5° C. $^1$H NMR (500 MHz J CDCl$_3$), δ 7.37-7.26 (m, 8H), 7.18-7.17 (m, 2H), 6.32 (d, J=9.0 Hz, 1H, NH), 4.24 (m, 1H), 4.11 (q, J=7.2 Hz, 2H) J 2.55 (b, 1H), 2.42 (b, 1H), 1.95 (b, 1H), 1.82 (b, 2H), 1.55 (b, 1H), 1.22 (s, 3H), 1.12 (d, J=7.2 Hz, 1H), 1.07 (d, J=7.1 Hz, 3H), 1.03 (t, J=7.2 Hz, 3H), 0.98 (s, 3H). $^{13}$C NMR (200 MHz, DMSO:CDCl$_3$=2:1, v/v), δ 159.7, 157.8, 141.9, 141.7, 129.3, 129.0, 125.5, 125.4, 119.4, 118.8, 111.6, 62.9, 48.7, 48.0, 46.7, 46.5, 41.7, 38.6, 35.5, 28.2, 23.5, 20.9, and 13.7 Anal. ($C_{28}H_{33}N_5O_3$) C, H, N.

N,N-Dipiperidinyl1,4-diphenyl-1,4-dihydro-1 2,4,5-tetrazine-3,6-dicarboxylic di-amide (5.45) and 1,4-Diphenyl-1,4-dihydro-1,2,4,5-tetrazine-3-carboxylic N-piperidinyl amide-6-carboxylic acid ethyl ester (5.58)

Using freshly distilled piperidine (from calcium hydride), the title compound was prepared analogously to 5.44 in 26% yield, mp 213-214° C. $^1$H NMR (500 MHz, CDCl$_3$) δ (ppm): 7.33-7.30 (m, 8H), 7.15-7.11 (m, 2H). 3.43 (m, 4H), 3-33 (m, 4H), 1.51 (m, 4H), 1.32 (m, 4H), 1.24 (m, 4H). $^{13}$C NMR (200 MHz, CDCl$_3$) δ (ppm): 159.1, 144.7, 141.3, 129.0, 125.2, 119.1, 47.5, 42.9, 26.0, 25.3, and 24.4. Anal. ($C_{26}H_{30}N_6O_2$) C, H, N. In the meanwhile, compound 5.58 was isolated in 12% yield. $^1$H NMR (500 MHz, CDCl$_3$) δ (ppm): 736-7.33 (m, 6H), 7.25-7.21 (m, 2H), 7.18-7.14 (m, 2H) 4.13 (q, J=7.1, 2H), 3.41 (b, 2H), 3.34 (b. 2H), 1.53 (b, 2H), 1.48 (b, 4H). 1.03 (t. J=7.1 Hz, 3H). Anal. ($C_{23}H_{25}N_5O_3$) C, H, N.

1-(4-chlorophenyl)-4-phenyl-1,4-dihydro-1,2,4,5-tetrazine-3,6-dicarboxylic acid diethyl ester (5.53)

Using a mixture of 5.6 and 5.12 (mole ratio=1:1) as starting material, the title compound was prepared analogously to the synthesis of 5.28 in 20% yield. $^1$H NMR (500 MHz. CDCl$_3$) δ (ppm): 7.37-7.18 (m, 9H) 4.19-4.09 (m, 4H), 1.12 (t, J;=12 Hz, 3H), 1.00 (t, J=12 Hz, 3H). $^{13}$C NMR (200 MHz, CDCl$_3$) δ (ppm): 159, 141, 140.1, 131, 129, 120, 63.2 and 13.8. Anal. ($C_{20}H_{19}ClN_4O_2$) C, H, N.

1-(4-Chlorophenyl)-4-(4-bromophenyl-1,4-dihydro-1,2,4,5-tetrazine-3,6-dicarboxylic acid diethyl ester (5.54)

Sodiohexamethyldisilazane (NaHMDS) (0.2 mL, 1 M solution in THF) was added dropwise to a solution of 5.12 (26.1 mg, 0.1 mmol) and 5.13 (30.5 mg, 0.1 mmol) in THF (0.5 mL) at −40° C. The reaction mixture changed from light yellow to reddish. After stirring for 2 h, the reaction was terminated by the addition of ammonium chloride aqueous solution, which followed by typical workup and silica gel flash column purification with petroleum ether:ethyl acetate (25: 1-10:1, v/v) as eluent provided the title compound 5.54 as an orange solid (36 mg. 73%), mp 130-131° C. HPLC was employed to examine the purity of 5.54: Beckman Gold System; silica gel normal phase column (Phenomenex, 250×10 mm), two eluent systems (1) ethanol:hexane=50:50-5:95 (v/v) gradient elution within 5 min, Rt=13 min; (2) ethyl acetate:hexane=10:90 (v/v) Rt=19 min. Under both eluent systems, a single sharp peak was obtained. $^1$H NMR (500 MHz, CDCl$_3$ δ (ppm): 7.49 (d, J=8.5 Hz, 2H), 7.34 (d, J=8.5 Hz, 2H), 7.23 (d, J=8.5 Hz, 2H), 7.17 (d, J=8.5 Hz, 1H), 4.17 (q, 4H), 1.10 (t, J=7.0 Hz. 6H). $^{13}$C NMR (500 MHz, CDCl$_3$) δ (ppm): 158.9, 141.3, 141.1, 140.3, 139.8, 123.1, 129.2, 120.1, 119.8, 118.4, 63.2, and 13.6.

1-Phenyl-4-α-naphthalenyl-1,4-dihydro-1,2,4,5-tetrazine-3,6-dicarboxylic acid diethyl ester (5.55)

Using 5.6 and 5.7 as starting material, the title compound was prepared analogously to the synthesis of 5.54 in 21% yield as a brown-red solid [silica gel purification with petroleum ether:ethyl acetate=15:1 (v/v)], mp 124-125° C. $^1$H NMR (200 MHz, CDCl$_3$) δ (ppm): 7.97-7.73 (m, 4H), 7.57-7.20 (m, 8H), 4.15 (q: J=7.0 Hz. 2H), 3.79 (q, J=7.4 Hz, 2H), 1.02 (t, J=7.0 Hz, 3H), 0.63 (t, J=7.4 Hz, 3H). $^{13}$C NMR (200 MHz, CDCl$_3$) δ (ppm): 159.8, 159.2, 143.3, 141.9, 138.2, 134-4, 129.3, 128.5, 128.3, 126.9, 126-6, 126.4, 125.9, 125.6, 122.3, 119.6, 118.9, 63.0, 62.6, 13.8, and 13.3. Anal. (C$_{24}$H$_{22}$N$_4$O$_4$) C, H, N.

1,4-Diphenyl-1,4-dihydro-1,2,4,5-tetrazine-3-aceto-6-carboxylic acid ethyl ester (5.56)

Using 5.6 and 5.18 as starting material, the title compound was prepared analogously to the synthesis of 5.54 in 8.6% yield. Silica gel flash column separated the symmetric product of 5.33 (from the dimerization of 5.18) and HPLC was employed to separate the title compound from 5.1 (from the dimerization of 5.6). HPLC separation conditions are as follows: silica gel normal phase column (Phenomenex, 250×10 mm); 2.5% ethyl acetate-hexane as eluent; Rt=32 min for 5.54 and 35.7 min for 5.1. $^1$H NMR (200 MHz, CDCl$_3$) δ (ppm): 7.30 (m, 10H), 4.14 (q, J=6.0 Hz, 2H), 2.49(s, 3H), 1.04 (t, J=7.0 Hz, 3H). $^{13}$C NMR (200 MHz, CDCl$_3$) δ (ppm): 159.8, 41.7, 129.4, 129.2, 125.7, 125.3, 119.1, 118.9, 118.7, 63.1, 28.7, and 13.8.

1,4-dihydro-1,2,3,4-tetrazine-3,6-dicarboxylic acid ester (5.62)

A three-necked flask containing 19 mL of dry ethanol was cooled to −30° C. and freshly distilled thionyl chloride (3 mL) was added dropwise. Dry dihydro-[1,2,4,5]tetrazine-3,6-dicarboxylic acid (2.86 g, 16.6 mmol) prepared according to the published procedure (Boger, et al, 1985) was suspended in 21 mL of dry ethanol and was added in two portions (over 15 min) to the stirred reaction mixture. The temperature was maintained at −30° C. during the additions. The reaction mixture was then allowed to warm to RT and subsequently was warmed at 35-40° C. (internal temperature) for 2 h. The mixture was cooled to 0° C. internal temperature with an ice bath and the precipitate collected by filtration. The precipitate was washed with 2 mL of dry methanol and 2 mL of dry ether, and dried under vacuum. Cooling the remaining mother liquor to −30° C. afforded a second smaller amount of product. The combined product was dissolved in anhydrous methylene chloride and filtered. After removal of the solvent, the filtrate afforded the title compound as an orange solid (1.5 g, 41%), mp 110-111° C. $^1$H NMR (200 MHz, CDCl$_3$) δ (ppm): 7.48 (s, 2H), 4.24 (q, J=7.2 Hz, 4H), 1.34 (t, J=7-2 Hz, 6H). Anal. (C$_{22}$H$_{12}$N$_4$O$_4$) C, H, N.

1,4-Di-(2-iodobenzoyl)-1,4-dihydro-1,2,4,5-tetrazine-3,6-dicarboxylic acid diethyl ester (5.64)

NaHMDS (1 mL, 1 M in THF) was added dropwise to a solution of 5.62 (114 mg, 0.5 mmol) in THF (5 mL) at −78° C., followed by the addition of 2-iodobenzoyl chloride (292.6 mg, 1.1 mmol). The reaction mixture first changed dark and then back to orange. After continuously stirring for 30 min at −78° C., the reaction was quenched by the addition of ammonium chloride aqueous solution. Standard workup and silica gel column purification (petroleum ether:ethyl acetate, 4:1, v/v) provided the title compound 5.64 (175 mg, 51%), mp 186-187° C. (recrystallization from ethyl acetate). $^1$H NMR (200 MHz, CDCl$_3$) δ 7.89 (d, J=7.8 Hz, 2H), 7.45-7.32 (m, 4H), 7.18 (td, J=1.5 Hz, J=7.6 Hz, 2H), 4.35 (q, J=7.2 Hz, 4H). 1.33 (t, J=7.2 Hz, 6H). Anal. (C$_{22}$H$_{18}$I$_2$N$_4$O$_6$) C, H, N.

1,4-Dibenzoyl-1,4-dihydro-1,2,4,5-tetrazine-3,6-dicarboxylic acid diethyl ester (5.63) and 1-Benzoyl-1,4-dihydro-1,2,4,5-tetrazine-3,6-dicarboxylic acid diethyl ester (5.65)

The title compound 5.63 was prepared analogously to the synthesis of 5.64 in 57% yield, and at the same time, the title compound 5.65 was isolated in 29% yield. For compound 5.63: mp 133.5-134° C. $^1$H NMR (200 MHz, CDCl$_3$) δ (ppm): 7.93-7.89 (m, 4H), 7.59-7.43 (m. 6H), 4.33 (q, J=7.0 Hz, 4H), 1.29 (t, J=7.0 Hz. 6H). Anal. (C$_{22}$H$_{20}$N$_4$O$_6$) C, H, N. For compound 5.65: mp 133-134° C. $^1$H NMR (200 MHz, CDCl$_3$) δ ppm): 8.35 (s, 1H), 7.85 (d, J=6-8 Hz, 2H), 7.54-7.41 (m. 3H), 4.36 (q, J=7.0 Hz, 4H), 1.27 (t, J=7.0 Hz, 6H).

Ethyl 5-oxo-2-phenyl-2,5-dihydroisoxazole-4-carboxylate (5.68)

Hydrazine hydrate (1.7 g) was added dropwise over 30 min to a stirred suspension of 5% Rh—C (wet, 110 mg) and nitrobenzene (4.1 g) in THF (20 mL) at 15° C. controlled by ice-bath. The reaction mixture was warmed to 25-30° C. for 2 h, followed by filtration. The filtrate was diluted with an equal volume of dichloromethane, dried over sodium sulfate, then condensed to a small volume. Addition of petroleum ether to this solution led to the formation of a needle-like white solid as the fairly pure product of phenyl hydroxyamine (3.2 g, 86%). The reaction mixture of phenyl hydroxyamine (2.675 g, 25 mmol), diethyl ethoxymethylene malonate (4.324 g, 20 mmol) and ethanol (20 mL) was stirred at RT for 12 h to form a large amount of solid, which after warming on a water-bath for 3 h disappeared and reappeared when the reaction mixture was cooled down to RT. Filtration and washing with ethanol provided the title compound as white crystal like solid (4.25 g, 91%). $^1$H NMR (200 MHz, CDCl$_3$) δ (ppm): 8.40 (s, 1H), 7.46-7.28 (m, 5H), 4.23(q, J=7.1 Hz, 2H). 1.31 (t, J.=7.1 Hz, 3H).

Ethyl (E)- and (Z)-2-chloro-3-phenylaminopropenoate (5.69)

The ester 5.68 (400 mg, 1.72 mmol) and triethylammonium chloride (710 mg, 5.16 mmol) were photolysed through Pyrex at 254 nm (using a 450 W Hanovia high pressure quartz mercury vapor lamp) in anhydrous acetonitrile (400 mL) under N$_2$ at RT. The reaction was followed by TLC (petroleum ether:ethyl acetate, 10:1, v/v) and was complete within 2 h. The solvent was removed under reduced pressure, and the residue was purified by silica gel flash column chromatography (petroleum ether:ethyl acetate, 20:-10:1, v/v) to afford the title compound (110 mg, 28.4%). $^1$H NMR (200 MHz, CDCl$_3$), δ (ppm): 11-02 (d, J=13.5 Hz, 1H), 8-53 (d, J=13.8 Hz, 1H), 737 (m, 2H), 7.15 (m, 3H), 4.27 (m, 2H), 135 (m, 3H). $^{13}$C NMR (200 MHz. CDCl$_3$), δ (ppm): 169.11, 165.76, 151-94, 139.39, 129.87, 129.33, 124.96, 117.26, 93.7, 60.37, 60.13, 14.52, and 14.41. GC-MS (EI), m/e: 225 (M$^+$), 179.

1,2,4,5-Tetrazine-3,6-dicarboxylic acid diethyl ester (5.71)

An aqueous solution of sodium nitrite (10 mL, 6N) was dropped into concentrated HCl (6.26 mL). The brown gas produced was driven by nitrogen gas into a solution of 5.62 (1.07 g, 4.7 mmol) in dichloromethane (40 mL), which was cooled with an ice/water bath. The gas was bubbled directly into the stirred reaction mixture for 15 min through a pippet. The color of the reaction mixture changed from orange to bright red during the bubbling of the NO gas. Stirring was continued for 1.5 h as the reaction mixture was warmed up to RT. The solvent and excess nitrous gases were removed under vacuum to afford the title compound (991 mg, 100%) as a rose-red crystalline solid, mp 85-90° C. $^1$H NMR (200 MHz, CDCl$_3$) δ (ppm): 4.68 (q, J=7.1 Hz, 4H), 1.54 (t, J=7.1 Hz, 6H). Anal. (C$_8$H$_{10}$N$_4$O$_4$) C, H, N.

Diethyl
5H-pyridazino-[4,5-b]-indole-1,4-dicarboxylate
(5.72)

To a solution of 5.71 (318 mg, 1.61 mmol) in anhydrous methylene chloride (15 mL) was added a solution of indole (100 mg, 0.85 mmol) in anhydrous methylene chloride (50 mL) dropwise over 4 h with stirring at mild reflux. Following the addition, stirring was continued for 4 h and the reaction mixture was then cooled down. After filtration, the filtrate was evaporated under (reduced pressure and the residue oil was submitted to chromatography (flash column, silica gel, methylene chloride:ethyl acetate=1:1, v/v as eluent) to afford the title compound 5.72 as an orange solid (132 mg, 52%), mp. 151-152° C. $^1$H NMR (200 MHz, CDCl$_3$) δ (ppm): 11.10 (s, 1H), 8-63 (d, J=8.2 Hz, 1H), 7.63 (d, J=7.6 Hz, 1H), 7.50 (t, J=7.0 Hz, 1H), 7.26 (t, J=7.0 Hz, 1H), 4.62 (q, J=7.0 Hz, 2H), 4.47 (q, J=7-0 Hz, 2H), 1.44 (I:, J=7.0 Hz, 3H), 1.34 (t, J=7.0 Hz, 3H). Anal. (C$_{16}$H$_{15}$N$_3$O$_4$) C, H, N.

1-Bromo-2,5-dimethyl-4-phenylbenzene (5.74) and
1,4-diphenyl-2,5-dimethyl-benzene (5.75)

Nitrogen gas was led to a solution of 2,5-dibromo-p-xylene (845 mg, 3.2 mmol) and phenylboronic acid (800 mg, 6.8 mmol) in toluene (25 mL) for 30 min followed by the addition of Palladium tetrakistriphenylphosphine (360 mg, 0.31 mmol) and potassium carbonate (1.0 g). The reaction mixture was heated to 85-100° C. for 24 h, followed by the removal of the solvent under vacuum. The residue was applied to silica gel flash chromatography with petroleum ether as solvent to afford the title compound 5.74 (435 mg, 52.1%) as an oil-like liquid and 5.75 (322 mg, 43.3%) as white solid. For compound 5.74: $^1$H NMR 200 MHz, CDCl$_3$) δ (ppm): 7.48-7.30 (m, 6H), 7.10 (s, 1H), 2.39 (s, 3H). 2.21 (s, 3H). GC-MS (EI), m/e: 262 (M$^+$+1), 260 (M$^+$−1), 178, 165, 152, 139, 128, 115, 102, 89, 76, 63, 51. For compound 5.75: mp 183-184° C. $^1$H NMR (200 MHz, CDCl$_3$) δ (ppm): 7.47-7.36 (m, 10H), 7.16 (s, 2H), 2.28 (s; 6H). GC-MS (EI), m/e: 258 M$^+$), 241, 228, 215, 202, 189, 178, 165, 152, 115, 91, 77, 63.51.

Diethyl 2,5-diphenyl-benzene-1,4-dicarboxylate
(5.77)

The reaction mixture of 5.75 (28 mg, 0.11 mmol), potassium permanganate (51.4 mg, 0.325 mmol), and potassium hydroxide (18.2 mg, 0.325 mmol) was heated at 100° C. for 24 h. After cooling down, the reaction mixture was filtrated and the filtrate was acidified by HCl (3N) to pH=1, followed by the extraction with ethyl acetate. After removal of the solvent, the organic layer afforded compound 2,5-diphenyl-1,4-dicarboxylic acid (5.76) as a white solid (15 mg, mixed with starting material).

Dried with P$_2$O$_5$, the above crude compound 5.76 was refluxed with thionyl chloride in toluene, followed by removal of the solvent under vacuum and reaction with ethanol to provide the title compound 5.77 (3.1 mg, 7.5% overall yield from 5.75). The low yield comes from the incomplete oxidation of 5.75 to 5.76). $^1$H NMR (200 MHz. CDCl$_3$) δ (ppm): 7.82 (s, 2H), 7.40-7.39 (m, 10H), 4.11 (q, J=7.1 Hz, 4H), 1.00 (t, J=7.1 Hz, 6H). GC-MS (EI), m/e: 374 (M$^+$), 329, 255, 226, 215, 150, 113, 77, 51.

The prepared cannabinoid compounds were tested for CB2 receptor binding affinity and for CB1 receptor affinity (to determine selectivity for the CB2 receptor). As used herein, "binding affinity" is represented by the IC$_{50}$ value which is the concentration of an analog required to occupy the 50% of the total number (Bmax) of the receptors. The lower the IC$_{50}$ value, the higher the binding affinity. As used herein a compound is said to have "binding selectivity" if it has higher binding affinity for one receptor compared to the other receptor; e.g. a compound that has an IC$_{50}$ of 0.1 nM for CB1 and 10 nM for CB2, is 100 times more selective for the CB1 receptor. The binding affinities (K$_i$) are expressed in nanomoles (nM).

For the CB1 receptor binding studies, membranes were prepared from rat forebrain membranes according to the procedure of P. R. Dodd et al; *A Rapid Method for Preparing Synaptosomes: Comparison with Alternative Procedures*, Brain Res., 107-118 (1981). The binding of the novel analogues to the CB1 cannabinoid receptor was assessed as described in W. A. Devane et al; *Determination and Characterization of a Cannabinoid Receptor in a Rat Brain*, Mol. Pharmacol., 34, 605-613 (1988) and A. Charalambous et al; "5'-azido $^8$-THC: A Novel Photoaffinity Label for the Cannabinoid Receptor", *J. Med. Chem.*, 35, 3076-3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM MgCl$_2$ and 1 mM EDTA) at a pH 7.4. The suspension was incubated at 40° C. for 30 min. At the end of the incubation, the membranes were pelleted and washed three times with TME.

The treated membranes were subsequently used in the binding assay described below. Approximately 30 μg of membranes were incubated in silanized 96-well microtiter plate with TME containing 0.1% essentially fatty acid-free bovine serum albumin (BSA), 0.8 nM [$^3$H] CP-55,940, and various concentrations of test materials at 30° C. for 1 hour. The samples were immediately filtered using a Packard Filtermate 196 and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield IC$_{50}$ values. Data from at least two independent experiments performed in duplicate was used to calculate IC$_{50}$ values which were converted to K$_i$ values using the using the assumptions of Cheng et al; "Relationship Between the Inhibition Constant (K$_i$) and the concentration of Inhibitor which causes 50% Inhibition (IC$_{50}$) of an Enzymatic Reaction", *Biochem. Pharmacol.*, 22, 3099-3102, (1973), which is incorporated by reference herein.

For the CB2 receptor binding studies, membranes were prepared from frozen mouse spleen essentially according to the procedure of P. R. Dodd et al; "A Rapid Method for Preparing Synaptosomes: Comparison with Alternative Procedures", *Brain Res.*, 226, 107-118 (1981) which is incorporated by reference herein. Silanized centrifuge tubes were used throughout to minimize receptor loss due to adsorption. The CB2 binding assay was conducted in the same manner as the CB1 binding assay. The binding affinities ($K_i$) were also expressed in nanomoles (nM). The structures, binding affinities and selectivities are summarized in Table 1.

Intracellular cyclic AMP (cAMP) levels are measured with a comparative protein binding assay (materials available from Diagnostic Products, Inc. of Carlsbad, Calif.) generally according to the method described in Tao, Q. and M. E. Abood; "Mutation of a highly conserved aspartate residue in the second transmembrane domain of the cannabinoid receptors, CB1 and CB2, disrupts G-protein coupling", *J Pharmacol Exp Ther*, 1998, 285(2): pp. 651-658, which is incorporated by reference herein. Using the above method compound 2 was found to reduce formation of cyclic AMP by inhibiting adenylate cyclase, indicating that compound 2, and the inventive compounds generally, function as CB2 agonists. The $IC_{50}$ value for Compound 2 was 8 nM.

The inventive compounds are unique in having a high affinity for the CB2 receptor and relatively little affinity for the CB1 receptor. As can be seen from Table 1, some of these compounds exhibit a high selectivity for the CB2 receptor of about 2 orders of magnitude.

While preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and scope of the present invention.

What is claimed is:

1. A cannabimimetic compound of Formula II below, and physiologically acceptable salts, diasteromers, enantiomers or double bond isomers of the compound:

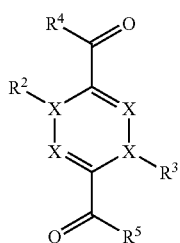

Formula II wherein each X is N;
$R^4$ is ethoxy;
$R^5$ is selected from methyl,

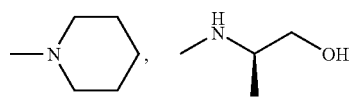

or an enantiomer thereof; and
$R^2$ and $R^3$ are each phenyl.

2. A cannabimimetic compound having Formula II below, and physiologically acceptable salts, diasteromers, enantiomers or double bond isomers of the compound:

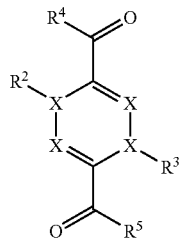

Formula II wherein each X is N;
$R^4$ and $R^5$ are each ethoxy;
$R^2$ is independently selected from phenyl, p-NO2 substituted phenyl, p-Cl substituted phenyl, p-Br substituted phenyl, p-OMe substituted phenyl, o, p-dichloro substituted phenyl, 1-naphthyl or phenyl ketone;
$R^3$ is independently selected from phenyl, p-NO2 substituted phenyl, p-Cl substituted phenyl, p-Br substituted phenyl, p-OMe substituted phenyl, o, p-dichloro substituted phenyl, 1-naphthyl or phenyl ketone;
with the proviso that $R^2$ and $R^3$ are not both p-NO2 substituted phenyl, p-Br substituted phenyl or p-OMe substituted phenyl.

3. The cannabimimetic compound of claim 2, wherein $R^2$ is phenyl; and $R^3$ is selected from p-Cl substituted phenyl or 1-naphthyl.

4. The cannabimimetic compound of claim 2, wherein $R^2$ is p-Br substituted phenyl; and $R^3$ is p-Cl substituted phenyl.

5. The cannabimimetic compound of claim 2, wherein $R^2$ and $R^3$ are each naphthyl.

6. A method of treating obesity in an animal or individual comprising administering to the individual or animal in need of such treatment a pharmaceutical preparation comprising a pharmaceutically acceptable carrier and an amount of a compound of Formula I below, and physiologically acceptable salts, diasteromers, enantiomers or double bond isomers of the compound:

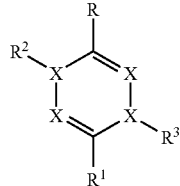

Formula I wherein:
X is N;
R is selected from $C_{1-6}$alkoxy; N-alkyl; S-alkyl; $C_{1-3}$haloalkoxy; $C_{1-6}$alkylketo; $C_{1-6}$alkylthioketo; $CO_2H$; $CONR^6R^7$ (where $R^6$ and $R^7$ are each independently selected from H, lower alkyl and carbalkoxyloweralkyl); or

wherein $R^4$ is selected from methoxy, ethoxy, propoxy, methyl, amino, methylamino, ethylamino, butylamino,

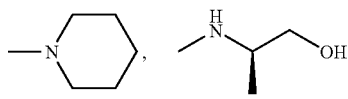

or an enantiomer thereof, or

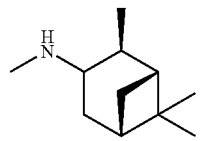

or an enantiomer thereof;

$R^1$ is selected from $C_{1-6}$alkoxy; N-alkyl; S-alkyl; $C_{1-3}$haloalkoxy; $C_{1-6}$alkylketo; $C_{1-6}$alkylthioketo; $CO_2H$; $CONR^6R^7$ where $R^6$ and $R^7$ are each independently selected from H, lower alkyl and carbalkoxyloweralkyl; or

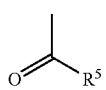

$R^5$ is selected from methoxy, ethoxy, propoxy, methyl, amino, methylamino, ethylamino, butylamino,

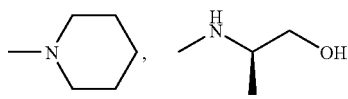

or an enantiomer thereof, or

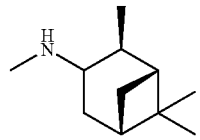

or an enantiomer thereof; and $R^2$ and $R^3$ are each independently selected from phenyl; benzyl; α-naphthyl; methylene-α-naphthyl; β-naphthyl; methylene-β-naphthyl; 5 or 6 membered heteroaromatic rings having 1 to 3 heteroatoms each independently selected from N, O, and S, provided that no more than 1 heteroatom is O or S; methylene-5 or 6 membered heteroaromatic rings having comprising 1 to 3 heteroatoms each independently selected from N, O, and S, provided that no more than 1 heteroatom is O or S; any of the above having up to 3 substituents independently selected from halo, hydroxyl, amino, lower alkyl amino, $C_{1-6}$alkyl, $C_{1-6}$alkoxy, $C_{1-6}$alkylthio, CN, $CF_3$, $CO_2H$, $CONR^6R^7$ (where $R^6$ and $R^7$ are each independently selected from H, lower alkyl or carbalkoxyloweralkyl), $SC_3H$, and $SO_2NR^6R^7$ (where $R^6$ and $R^7$ are each independently selected from H, lower alkyl or carbalkoxyloweralkyl); $C_{1-10}$alkyl; 1,1-dimethyl alkyl or 1,1-dimethyl alkoxy.

7. A method of preparing a tetrazine analog, comprising any of routes a-d:

Scheme I

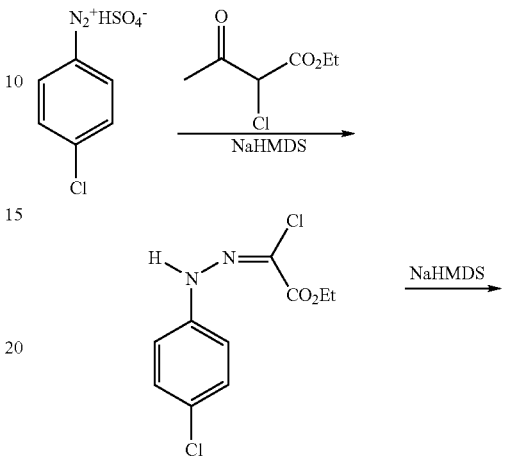

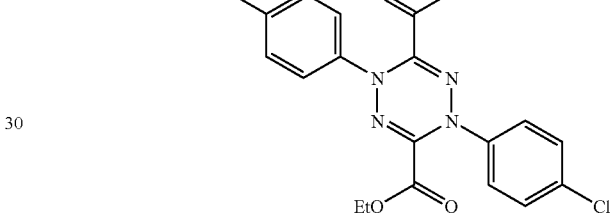

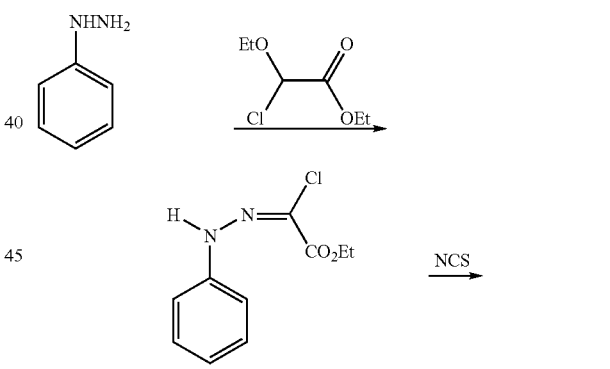

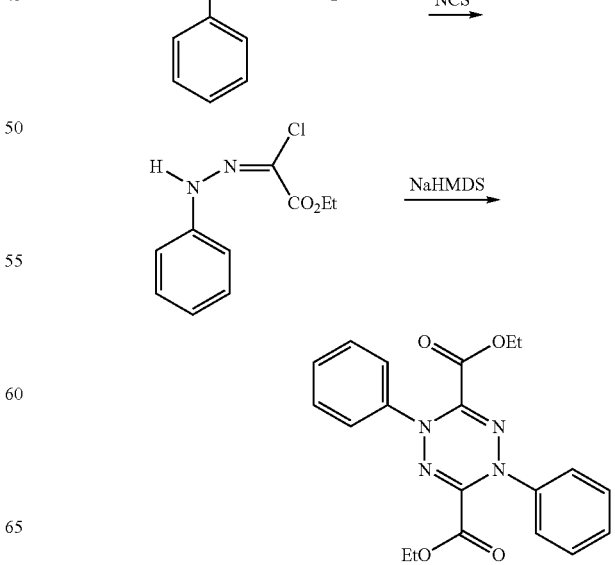

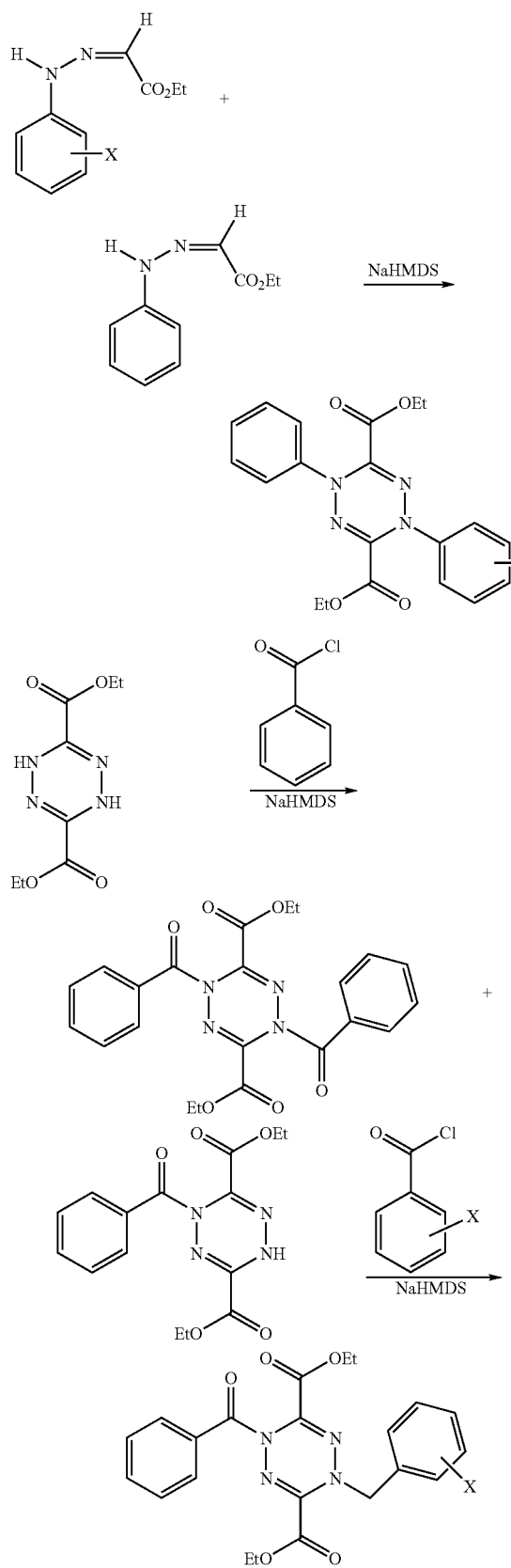

8. The method of claim 7 wherein the prepared tetrazine analog is a cannabinoid compound.

9. The method of claim 7 wherein the prepared tetrazine analog is a CB2 selective cannabinoid compound.

10. A pharmaceutical preparation comprising:
a therapeutically effective amount of a compound of claim 2 and physiologically acceptable salts, diasteromers, enantiomers or double bond isomers of the compound and a pharmaceutically acceptable carrier.

11. The method of claim 6 comprising administering to the individual or animal in need of such treatment an amount of a compound of Formula II below, and physiologically acceptable salts, diasteromers, enantiomers or double bond isomers of the compound:

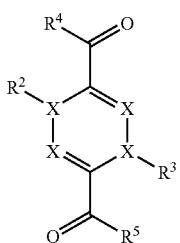

Formula II wherein:
$R^4$ and $R^5$ are each independently selected from methoxy, ethoxy, propoxy, methyl, amino, methylamino, ethylamino, butylamino,

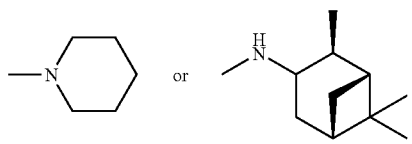

or an enantiomer thereof, or

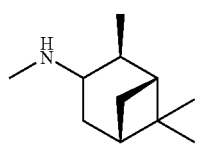

or an enantiomer thereof; and
$R^2$ and $R^3$ are each phenyl.

12. A pharmaceutical preparation comprising:
a therapeutically effective amount of a compound of claim 1 and physiologically acceptable salts, diasteromers, enantiomers or double bond isomers of the compound and a pharmaceutically acceptable carrier.

* * * * *

UNITED STATES PATENT AND TRADEMARK OFFICE
CERTIFICATE OF CORRECTION

PATENT NO.        : 7,329,651 B2                                                   Page 1 of 2
APPLICATION NO.   : 10/466403
DATED             : February 12, 2008
INVENTOR(S)       : Makriyannis et al.

It is certified that error appears in the above-identified patent and that said Letters Patent is hereby corrected as shown below:

Column 23:

Lines 57 - 61, delete: "  "

and substitute: -- 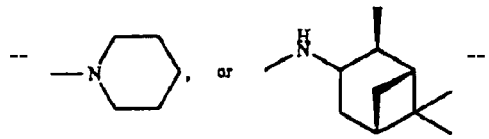 --

Column 25:

Line 64, delete "SC$_3$H," and substitute --SO$_3$H,--.

Column 26:

Line 5, delete "Scheme I".

Column 26:

Lines 42 - 48, delete: " 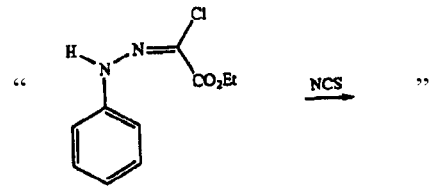 "

and substitute: -- 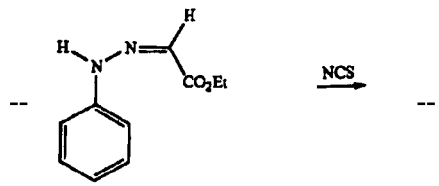 --

Column 27:

Lines 11 - 18, delete: " 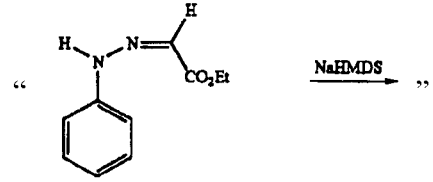 "

and substitute: -- 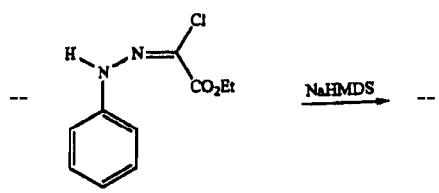 --

UNITED STATES PATENT AND TRADEMARK OFFICE
CERTIFICATE OF CORRECTION

PATENT NO. : 7,329,651 B2  Page 2 of 2
APPLICATION NO. : 10/466403
DATED : February 12, 2008
INVENTOR(S) : Makriyannis et al.

It is certified that error appears in the above-identified patent and that said Letters Patent is hereby corrected as shown below:

Column 27:

Lines 57 - 65, delete: " 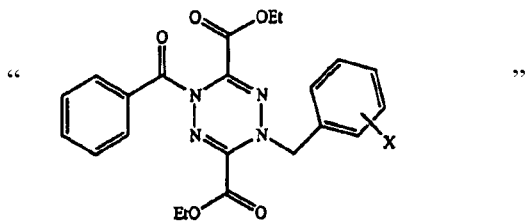 "

and substitute: -- 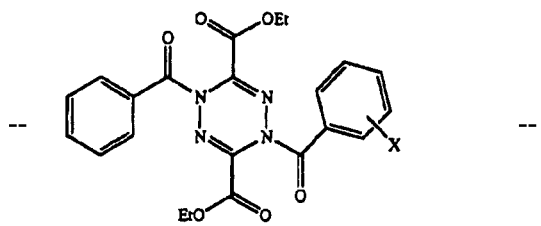 --

Column 28:

Lines 39 - 44, delete: " 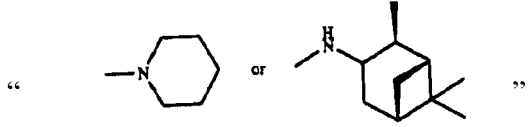 "

and substitute: -- 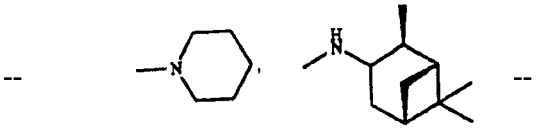 --

Signed and Sealed this

Second Day of September, 2008

JON W. DUDAS
*Director of the United States Patent and Trademark Office*